(12) United States Patent
Goeddel et al.

(10) Patent No.: US 7,754,858 B2
(45) Date of Patent: Jul. 13, 2010

(54) ANTIBODIES TO TUMOR NECROSIS FACTOR RECEPTOR ASSOCIATED FACTOR POLYPEPTIDES

(75) Inventors: David V. Goeddel, Hillsborough, CA (US); Mike Rothe, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/759,405

(22) Filed: Jun. 7, 2007

(65) Prior Publication Data

US 2007/0243202 A1 Oct. 18, 2007

Related U.S. Application Data

(63) Continuation of application No. 10/283,500, filed on Oct. 30, 2002, now Pat. No. 7,244,836, which is a continuation of application No. 08/779,599, filed on Jan. 7, 1997, now Pat. No. 6,500,922, which is a continuation of application No. 08/744,139, filed on Nov. 5, 1996, now Pat. No. 5,869,612, which is a continuation of application No. 08/250,858, filed on May 27, 1994, now Pat. No. 5,708,142.

(51) Int. Cl.
 *A61K 39/00* (2006.01)
 *C07K 16/44* (2006.01)
 *C12N 5/20* (2006.01)

(52) U.S. Cl. .................. 530/387.9; 424/139.1; 435/331

(58) Field of Classification Search ........................ None
See application file for complete search history.

(56) References Cited

U.S. PATENT DOCUMENTS

| | | | |
|---|---|---|---|
| 4,861,587 A | 8/1989 | Urbaschek et al. | |
| 5,670,319 A | 9/1997 | Goeddel | |
| 5,708,142 A | 1/1998 | Goeddel et al. | |
| 5,741,667 A | 4/1998 | Goeddel et al. | |
| 5,869,612 A | 2/1999 | Goeddel et al. | |
| 6,500,922 B1 | 12/2002 | Goeddel et al. | |

OTHER PUBLICATIONS

Alberts, et al., *Molecular Biology of the Cell* - 3rd editon, New York & London:Garland Publishing, Inc., Chapter 15, pp. 761-762 (1994).
Bazan, F., *Current Biology* - 3(9):603-606 (1993).
Berberich, et al., *The Journal of Immunology* - 153:4357-4366 (1994).
Cheng, et al., Science - 267(8):1494-1498 (1995).
Chien, et al., *Proc. Natl. Acad. Sci. USA* - 88:9578-9582 (1991).
Durfee, et al., *Genes and Development* - 7(4):555-569 (1993).
Hu, et al., *Journal of Biological Chemistry* - 269(48):30069-30072 (1994).
Huen, et al., *Oncogene* 10:549.560 (1995).
Mosialos, et al., *Cell* -80:389-399 (1995).
Rothe, et al., *Cell* - 78:681.692 (1994).
Sato, et al., *FEBS Letters* - 358 2 :113-118 (1995).
Smith, et al., *Cell* - 76:959-962 (1994).
Tartaglia, et al., *Cell* - 75(5):845-853 (1993).
Vanarsdale, et al., "Ligand-dependent stimulation of a serine protein kinase activity associated with (CD120a) TNFR601", The journal of Immunology, pp. 3043-3050, (1994).
Goeddel, et al., "Signaling in TNF receptors", Journal of cellular biochemistry supplement, vol. 0, No. 18B, p. 203, (1994).

*Primary Examiner*—John D Ulm
(74) *Attorney, Agent, or Firm*—Elizabeth M. Barnes; Ginger R. Dreger; Arnold & Porter LLP

(57) ABSTRACT

The invention concerns antibodies to new tumor necrosis factor receptor associated factors, designated TRAF. The new factors are capable of specific association with the intracellular domain of the type 2 TNF receptor (TNF-R2), and are involved in the mediation of tumor necrosis factor (TNF) biological activities.

2 Claims, 16 Drawing Sheets

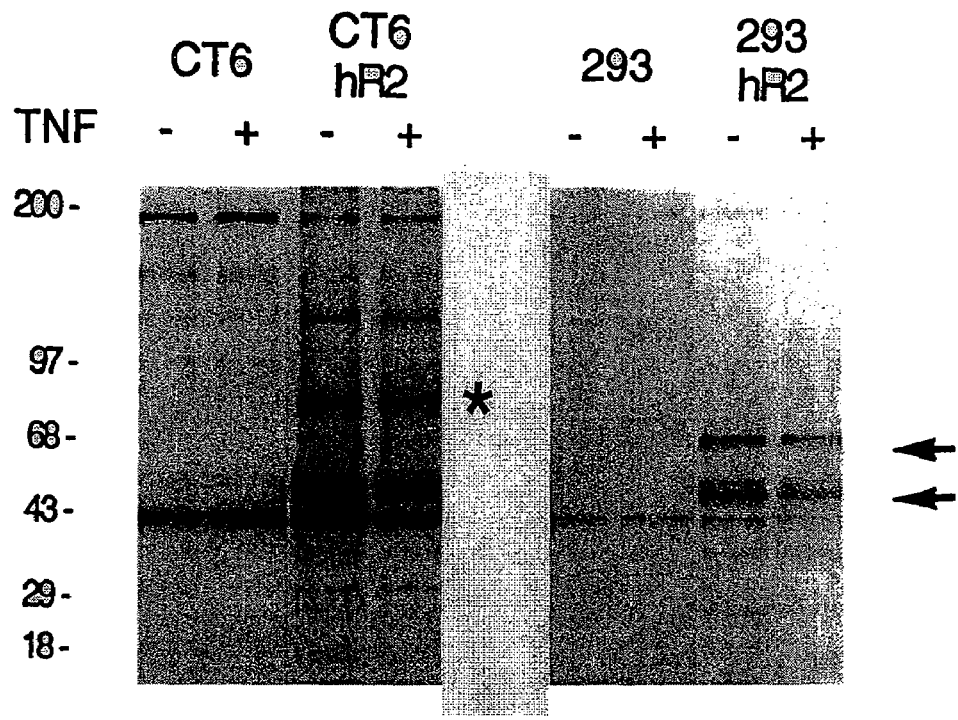
FIG. 2A      FIG. 2B
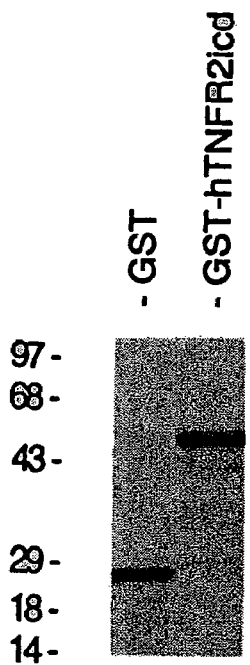
FIG. 3

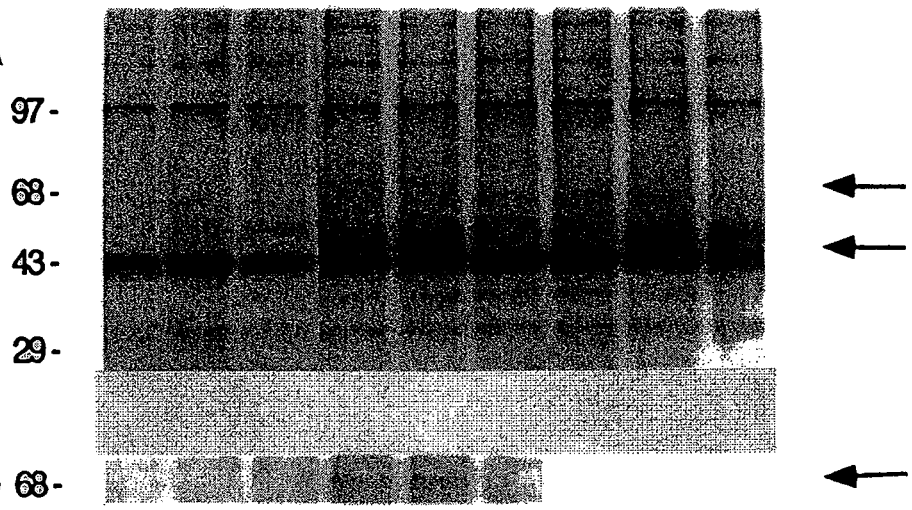
FIG. 6A
FIG. 6B
CT6
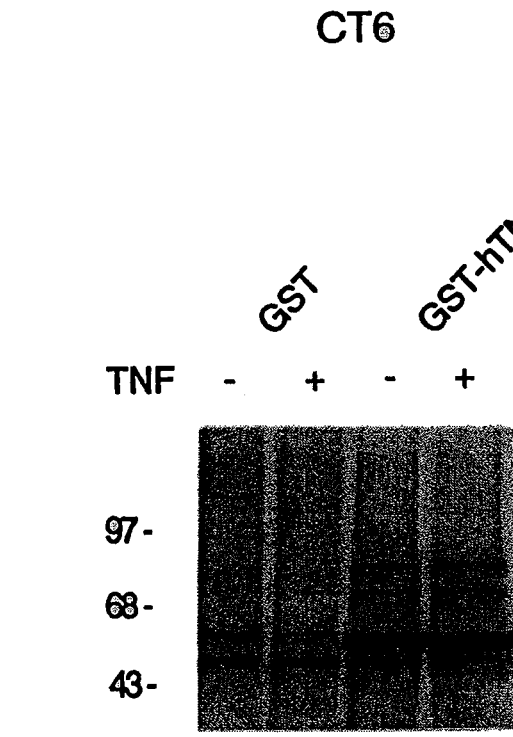
FIG. 7

| | | | | |
|---|---|---|---|---|
| TRAF2 (mouse) | 31 | KYLCsaCKNILRRPFQA QCGHRYCSFCLTSI | LSS | GPQNCAACVYE |
| COP1 (A. thaliana) | 49 | DLLCPICMQIIKDAFLT ACGHSFCYMCIITH | LRN | KSDCPCCSQH |
| EFP (human) | 10 | ELSCSICLEPFKEPVTT PCGHNFCGSCLNETWA | VQG | SPYLCPQCRAV |
| RAD-18 (S. cerevisiae) | 25 | LLRCHICKDFLKVPVLT PCGHTFCSLCIRTH | LNN | QPNCPLCLFE |
| UVS-2 (N. crassa) | 31 | AFRCHVCKDFYDSPMLT SCNHTFCSLCIRRC | LSV DSK | CPLCRAT |
| RAG-1 (human) | 290 | SISCQICEHILADPVET NCKHVFCRVCILRC | LKV | MGSYCPSCRYP |
| SS-A/Ro (human) | 13 | EVTCPICLDPFVEPVSI ECGHSFCQECISQV | GKG | GGSVCAVCRQR |
| RING1 (human) | 16 | ELMCPICLDMLKNTMTKECLERFCSDCIVTA | LRS | GNKECPTCRKK |
| RPT-1 (mouse) | 12 | EVTCPICLELLKEPVSA DCNHSFCRACITLNYESNRNTDGKGNCPVCRVP | | |
| RFP (human) | 13 | ETTCPVCLQYFAEPMML DCGHNICCACLARCWGTA | | ETNVSCPQCRET |
| c-cbl (human) | 378 | FQLCKICAENDKDVKIE PCGHLMCTSCLTS WQESEGQ | | GSSGCPFCRCE | consensus ---C--C-----------C-H-C--C----X11-12----------C--C---X10-16

FIG. 12B

| | | | |
|---|---|---|---|
| TRAF2 | (mouse) | 157 | CPKRSLSCQHC RAPCSHVDLEVHYE vC |
| | | 182 | PKFPLTCDGCGKKKIPRETFQDHVR AC |
| DG17 | (D. discoideum) | 171 | GGFKLVTCDFCKRDDIKKKELETHYK TC |
| TFIIIA | (X. laevis) | 189 | QD LAVCDVCNRKFRHKDYLRDHQK TH |
| XLCOF14 | (X. laevis) | 1 | TGKYPFICSECGKSFMDKRYLKIHSN vH |
| XFIN | (X. laevis) | 1225 | TGEKPYTCTVCGKKFIDRSSVVKHSR TH |
| ZFY1/2 | (mouse) | 521 | RKKFPHICGECGKGFRHPSALKKHIR vH |
| MFG2 | (mouse) | 293 | SEEKPFECEECGKKFRTARHLVKHQR iH |
| RAD18 | (S. cerevisiae) | 183 | PNEQMAQCPICQQFYPLKALEKTHLD eC |
| UVS-2 | (N. crassa) | 182 | PDDGLVACPICLTRM KEQQVDRHLDTSC |

TRAF2    1   M A A A S V T S P G S L E L L Q P G F S K T L L G T R L E A K Y L C S A C K N I L R R P F Q A Q C G

TRAF2   51   H R Y C S F C L T S I L S S G P Q N C A A C V Y E G L Y E E G I S I L E S S S A F P D N A A R R E V

TRAF2   101  E S L P A V C P N D G C T W K G T L K E Y E S C H E G L C P F L L T E C P A C K G L V R L S E K E H
TRAF1    1   - - - - - - - - - - - - - - - - - - - - - - - - - - - M A S S S A P D E N E F Q F G C P P A

TRAF2   151  H T E Q E C P K R S L S C Q H C R A P C S H V D L E V H Y E V C P K F P L T C D G C G K K K I P R E
TRAF1   20   P C Q D P S E P R V L C C T A C L S E N L R D D E D R I C P K C R A D N L H P V S P G - S P L T Q E

TRAF2   201  T F Q D H V R A C S K C R V L C R F H T V G C S E M V E T E N L Q D H E L Q R L R E H L A L L L S S
TRAF1   69   K V H S D V - - - A E A E I M C P F A G V G C S F K G S P Q S M Q E H E A T S Q S S H L Y L L L A V

TRAF2   251  F L E A Q A S P G T L N Q V G P E L L Q R - - - - - - - - - - - - - - -
TRAF1   116  L K E W K S S P G S N L G S A P M A L E R N L S E L Q L Q A A V E A T G ⁻ E V D C Y R A P C C E S

TRAF2   272  - - - - - - - - - - - - - - C Q I L E Q K I A T F E N I V C V L N R E V E R V A V T A E A C S R Q H
TRAF1   166  Q E E L A L Q H L V K E K L L A Q L E E K L R V F A N I V A V L N K E V E A S H L A L A A S I H Q S

TRAF2   308  R L D Q Q K I E A L S N K V Q Q L E R S I G L K D L A M A D L E Q K V S E L E V S T Y D G V F I W K
TRAF1   216  Q L D R E H L L S L E Q R V V E L Q Q T L A Q K D Q V L G K L E H S L R L M E E A S F D G T F L W K

TRAF2   358  I S D F T R K R Q E A V A G R T P A I F S P A F Y T S R Y G Y K M C L R V Y L N G D G T G R G T H L
TRAF1   266  I T N V T K R C H E S V C G R T V S L F S P A F Y T A K Y G Y K L C L R L Y L N G D G S G K K T H L

TRAF2   408  S L F F V V M K G P N D A L L Q W P F N Q K V T L M L L D H N N R E H V I D A F R P D V T S S S F Q
TRAF1   316  S L F I V I M R G E Y D A L L P W P F R N K V T F M L L D Q N N R E H A I D A F R P D L S S A S F Q

TRAF2   458  R P V S Q M N I A S G C P L F C P V S K M E   A K N S Y V R D D A I F I K A I V D L T G L
TRAF1   366  R P Q S E T N V A S G C P L F F P L S K L Q S P K H A Y V K D D T M F L K C I V D T S A

FIG. 13

SEQUENCE LISTING (1) GENERAL INFORMATION:

(iii) NUMBER OF SEQUENCES: 59

(2) INFORMATION FOR SEQ ID NO: 1:

(i) SEQUENCE CHARACTERISTICS:
      (A) LENGTH: 2088 base pairs
      (B) TYPE: Nucleic Acid
      (C) STRANDEDNESS: Single
      (D) TOPOLOGY: Linear (xi) SEQUENCE DESCRIPTION: SEQ ID NO: 1:

```
CCCAGCCCGG TTCTCTGCCC CAAGGACGCT ACCGCCCAAT GCGAGCAGAA           50

GGCGGCGCAC AGATACAGAA AGTGAGGCTC AGACATATTG AAGACCGTGT          100

GACATAGGGT AGCCAAATGA CAGTGTGAGA AAGTGACATT TACTCAAGGC          150

CACCCAGATA TCCTGGAGGA CCCAGAACCC TGGAGATTCC CATCAGAAAG          200

ACCTTCTGGC CACCTGAAAC CCCAAGATGG CCTCCAGCTC AGCCCCTGAT          250

GAAAACGAGT TTCAATTTGG TTGCCCCCCT GCTCCCTGCC AGGACCCATC          300

GGAGCCCAGA GTTCTCTGCT GCACAGCCTG TCTCTCTGAG AACCTGAGAG          350

ATGATGAGGA TCGGATCTGT CCTAAATGCA GAGCAGACAA CCTCCATCCT          400

GTGAGCCCAG GAAGCCCTCT GACTCAGGAG AAGGTTCACT CTGATGTAGC          450

TGAGGCTGAA ATCATGTGCC CCTTTGCAGG TGTTGGCTGT TCCTTCAAGG          500

GGAGCCCACA ATCCATGCAG GAGCATGAGG CTACCTCCCA GTCCTCCCAC          550

CTGTACCTGC TGCTGGCGGT CTTAAAGGAG TGGAAATCCT CACCAGGCTC          600

CAACCTAGGG TCTGCACCCA TGGCACTGGA GCGGAACCTG TCAGAGCTGC          650

AGCTTCAGGC AGCTGTGGAA GCGACAGGGG ACCTGGAGGT AGACTGCTAC          700

CGGGCACCTT GCTGTGAGAG CCAGGAAGAA CTGGCCCTGC AGCACTTGGT          750
```

-continued

```
GAAGGAGAAG CTGCTGGCTC AGCTGGAGGA GAAGCTGCGT GTGTTTGCAA        800

ACATTGTTGC TGTCCTCAAC AAGGAAGTGG AGGCTTCCCA CCTGGCACTG        850

GCCGCCTCCA TCCACCAGAG CCAGTTGGAC CGAGAGCACC TCCTGAGCTT        900

GGAGCAGAGG GTGGTGGAAT TACAGCAAAC CCTGGCTCAA AAAGACCAGG        950

TCCTGGGCAA GCTTGAGCAC AGTCTGCGAC TCATGGAGGA GGCATCCTTT       1000

GATGGTACTT TCCTGTGGAA GATCACCAAT GTCACCAAGC GGTGCCACGA       1050

GTCAGTGTGT GGCCGGACTG TCAGCCTCTT CTCTCCAGCT TTCTACACTG       1100

CCAAGTATGG TTACAAGTTG TGCCTGCGCT TGTACCTGAA CGGGGATGGC       1150

TCAGGCAAGA AGACCCACCT GTCCCTCTTC ATCGTGATCA TGAGAGGAGA       1200

ATACGATGCT CTCCTGCCCT GGCCTTTCAG GAACAAGGTC ACCTTTATGC       1250

TACTTGACCA AACAACCGA GAGCATGCTA TTGATGCCTT CCGGCCTGAC        1300

CTGAGCTCAG CCTCCTTCCA GCGGCCACAG AGTGAGACCA ACGTGGCCAG       1350

CGGCTGCCCG CTCTTCTTCC CCCTCAGCAA GCTGCAGTCA CCCAAGCACG       1400

CCTACGTCAA AGATGACACA ATGTTCCTCA AATGCATTGT GGACACTAGT       1450

GCTTAGGGAT GGGGGGAGGG GGTGTCTCCT GACAGAACCA GCTTAGACTG       1500

GGGGACTTAG CTAGACAGCC AGGCCCTGCC TGCCCTTGGA GCCCACAGCC       1550

CACGACAAGG AGGAGCCAAG GCTGGCATGA CTTCAGCGCC ACAGCATGCT       1600

GGTTATGGCT GATGTGAGGC TGGAGAAACG TGTGCGTACA GAGACAGAGT       1650

GGAGGAGAAG ACAGAAGTGC TCTTTTCACA CAGACTACAC GACACCAGGA       1700

GGCCAGCATG CCAGCAGCTT CTGAATGTTG AGACCAGCCT AGATCAGGAT       1750

GAAAAGAGCC AGGCCTGAGG CTTGGACATT GAGCCAAGGC TATGGGGCCT       1800

AAGTGGAGGG GCACTCCTAC CAGGACATTC TCTCGAGGTC AGGGCATAAC       1850

TGGAAAAATG CCCCCATCTC TCTGTTCAGA CTCAAAACTA GAACCACAGG       1900

GCAGAAGGGT CAGACATTAA TGTGAATTTA ACCTGCCCTG GACTGAGTTC       1950

CTATGTTAAC AGACACGCAA ACAGGTAAAC CCAGAAACTG CCCTGGGAAA       2000

TGCTTTCTGG CTGCATCTGG AGATCTTTGA TGTTTTTACC GACAAAACAA       2050

ATAACAAAAG CCTTGAATTG CAAAAAAAAA AAAAAAA                    2088
```

(2) INFORMATION FOR SEQ ID NO: 2:

(i) SEQUENCE CHARACTERISTICS:
        (A) LENGTH: 409 amino acids
        (B) TYPE: Amino Acid
        (D) TOPOLOGY: Linear (xi) SEQUENCE DESCRIPTION: SEQ ID NO: 2:

```
Met Ala Ser Ser Ala Pro Asp Glu Asn Glu Phe Gln Phe Gly
 1               5                  10                  15

Cys Pro Pro Ala Pro Cys Gln Asp Pro Ser Glu Pro Arg Val Leu
                20                  25                  30

Cys Cys Thr Ala Cys Leu Ser Glu Asn Leu Arg Asp Asp Glu Asp
                35                  40                  45

Arg Ile Cys Pro Lys Cys Arg Ala Asp Asn Leu His Pro Val Ser
                50                  55                  60

Pro Gly Ser Pro Leu Thr Gln Glu Lys Val His Ser Asp Val Ala
                65                  70                  75
```

```
Glu Ala Glu Ile Met Cys Pro Phe Ala Gly Val Gly Cys Ser Phe
                80                  85                  90

Lys Gly Ser Pro Gln Ser Met Gln Glu His Glu Ala Thr Ser Gln
                95                 100                 105

Ser Ser His Leu Tyr Leu Leu Leu Ala Val Leu Lys Glu Trp Lys
               110                 115                 120

Ser Ser Pro Gly Ser Asn Leu Gly Ser Ala Pro Met Ala Leu Glu
               125                 130                 135

Arg Asn Leu Ser Glu Leu Gln Leu Gln Ala Ala Val Glu Ala Thr
               140                 145                 150

Gly Asp Leu Glu Val Asp Cys Tyr Arg Ala Pro Cys Cys Glu Ser
               155                 160                 165

Gln Glu Glu Leu Ala Leu Gln His Leu Val Lys Glu Lys Leu Leu
               170                 175                 180

Ala Gln Leu Glu Glu Lys Leu Arg Val Phe Ala Asn Ile Val Ala
               185                 190                 195

Val Leu Asn Lys Glu Val Glu Ala Ser His Leu Ala Leu Ala Ala
               200                 205                 210

Ser Ile His Gln Ser Gln Leu Asp Arg Glu His Leu Leu Ser Leu
               215                 220                 225

Glu Gln Arg Val Val Glu Leu Gln Gln Thr Leu Ala Gln Lys Asp
               230                 235                 240

Gln Val Leu Gly Lys Leu Glu His Ser Leu Arg Leu Met Glu Glu
               245                 250                 255

Ala Ser Phe Asp Gly Thr Phe Leu Trp Lys Ile Thr Asn Val Thr
               260                 265                 270

Lys Arg Cys His Glu Ser Val Cys Gly Arg Thr Val Ser Leu Phe
               275                 280                 285

Ser Pro Ala Phe Tyr Thr Ala Lys Tyr Gly Tyr Lys Leu Cys Leu
               290                 295                 300

Arg Leu Tyr Leu Asn Gly Asp Gly Ser Gly Lys Lys Thr His Leu
               305                 310                 315

Ser Leu Phe Ile Val Ile Met Arg Gly Glu Tyr Asp Ala Leu Leu
               320                 325                 330

Pro Trp Pro Phe Arg Asn Lys Val Thr Phe Met Leu Leu Asp Gln
               335                 340                 345

Asn Asn Arg Glu His Ala Ile Asp Ala Phe Arg Pro Asp Leu Ser
               350                 355                 360

Ser Ala Ser Phe Gln Arg Pro Gln Ser Glu Thr Asn Val Ala Ser
               365                 370                 375

Gly Cys Pro Leu Phe Phe Pro Leu Ser Lys Leu Gln Ser Pro Lys
               380                 385                 390

His Ala Tyr Val Lys Asp Asp Thr Met Phe Leu Lys Cys Ile Val
               395                 400                 405

Asp Thr Ser Ala (2) INFORMATION FOR SEQ ID NO: 3:

(i) SEQUENCE CHARACTERISTICS:
        (A) LENGTH: 2121 base pairs
        (B) TYPE: Nucleic Acid
        (C) STRANDEDNESS: Single
        (D) TOPOLOGY: Linear (xi) SEQUENCE DESCRIPTION: SEQ ID NO: 3:
```

| | |
|---|---:|
| GCGCGAAGAC CGTTGGGGCT TTGTGGTGTG TGGGGGTTGT AACTCACATG | 50 |
| GCTGCAGCCA GTGTGACTTC CCCTGGCTCC CTAGAACTGC TACAGCCTGG | 100 |
| CTTCTCCAAG ACCCTCCTGG GGACCAGGTT AGAAGCCAAG TACCTCTGTT | 150 |
| CAGCCTGCAA AAACATCCTG CGGAGGCCTT TCCAGGCCCA GTGTGGGCAC | 200 |
| CGCTACTGCT CCTTCTGCCT GACCAGCATC CTCAGCTCTG GCCCCAGAA | 250 |
| CTGTGCTGCC TGTGTCTATG AAGGCCTGTA TGAAGAAGGC ATTTCTATTT | 300 |
| TAGAGAGTAG TTCGGCCTTT CCAGATAACG CTGCCCGCAG AGAGGTGGAG | 350 |
| AGCCTGCCAG CTGTCTGTCC CAATGATGGA TGCACTTGGA AGGGGACCTT | 400 |
| GAAAGAATAC GAGAGCTGCC ACGAAGGACT TGCCCATTC CTGCTGACGG | 450 |
| AGTGTCCTGC ATGTAAAGGC CTGGTCCGCC TCAGCGAGAA GGAGCACCAC | 500 |
| ACTGAGCAGG AATGCCCCAA AAGGAGCCTG AGCTGCCAGC ACTGCAGAGC | 550 |
| ACCCTGTAGC CACGTGGACC TGGAGGTACA CTATGAGGTC TGCCCCAAGT | 600 |
| TTCCCTTAAC CTGTGATGGC TGTGGCAAGA AGAAGATCCC TCGGGAGACG | 650 |
| TTTCAGGACC ATGTTAGAGC ATGCAGCAAA TGCCGGGTTC TCTGCAGATT | 700 |
| CCACACCGTT GGCTGTTCAG AGATGGTGGA GACTGAGAAC CTGCAGGATC | 750 |
| ATGAGCTGCA GCGGCTACGG GAACACCTAG CCCTACTGCT GAGCTCATTC | 800 |
| TTGGAGGCCC AAGCCTCTCC AGGAACCTTG AACCAGGTGG GGCCAGAGCT | 850 |
| ACTCCAGCGG TGCCAGATTT TGGAGCAGAA GATAGCAACC TTTGAGAACA | 900 |
| TTGTCTGCGT CTTGAACCGT GAAGTAGAGA GGGTAGCAGT GACTGCAGAG | 950 |
| GCTTGTAGCC GGCAGCACCG GCTAGACCAG GACAAGATTG AGGCCCTGAG | 1000 |
| TAACAAGGTG CAACAGCTGG AGAGGAGCAT CGGCCTCAAG GACCTGGCCA | 1050 |
| TGGCTGACCT GGAGCAGAAG GTCTCCGAGT TGGAAGTATC CACCTATGAT | 1100 |
| GGGGTCTTCA TCTGGAAGAT CTCTGACTTC ACCAGAAAGC GTCAGGAAGC | 1150 |
| CGTAGCTGGC CGGACACCAG CTATCTTCTC CCCAGCCTTC TACACAAGCA | 1200 |
| GATATGGCTA CAAGATGTGT CTACGAGTCT ACTTGAATGG CGACGGCACT | 1250 |
| GGGCGGGAA CTCATCTGTC TCTCTTCTTC GTGGTGATGA AAGGCCCCAA | 1300 |
| TGATGCTCTG TTGCAGTGGC CTTTTAATCA GAAGGTAACA TTGATGTTGC | 1350 |
| TGGACCATAA CAACCGGGAG CATGTGATCG ACGCATTCAG GCCCGATGTA | 1400 |
| ACCTCGTCCT CCTTCCAGAG GCCTGTCAGT GACATGAACA TCGCCAGTGG | 1450 |
| CTGCCCCCTC TTCTGCCCTG TGTCCAAGAT GGAGGCCAAG AATTCCTATG | 1500 |
| TGCGGGATGA TGCGATCTTC ATCAAAGCTA TTGTGGACCT AACAGGACTC | 1550 |
| TAGCCACCCC TGCTAAGAAT AGCAGCTCAG TGAGGAGCTG TCACATTAGG | 1600 |
| CCAGCCAGGC CCTGCCACAC ACGGGTGGGC AGGCTTGGTG TAAATGCTGG | 1650 |
| GGAGGGCCTC AGCCTAGAGC CAATCACCAT CACACAGAAA GGCAGGAAGA | 1700 |
| AGCCTCCAGT TGGCCTTCAG CTGGCAAACT GAGTTGGACG GTCCACTGAG | 1750 |
| CTCAAGGGCC TGGTGGAGCC CGCTGGGGAG CTTCTCAGCT TTCCAATAGG | 1800 |
| AAAGCTCCTG CTGTCTCCTC TGTCTGGGGA AGGGAGAGAC CTGTAGGTGG | 1850 |
| GTGCTCAGAA AGGGCCTCTC CAGAGAGAGT CTCAAGAGCT GCAGCAGGAG | 1900 |
| CAAAGTGACT GGCCTTCCCC ACCCCATCCT TTGGAAAAGA GGTAGCGGCT | 1950 |
| ACACAGGAGA AGGCATGCGC CTGCAGGGTG TAGCCCAAGA GAGAAGCTCT | 2000 |

-continued

```
CTGAGACATA GGCCCTCACT GGAGAAGGGC CTGCCTGGGC TGCACAGCCT        2050

TGCCAGGTGG CCTGTATGGG GGAGAAGTGA TTAAATGTTG AGATGTCACA        2100

CGACAAAAAA AAAAAAAAAA A                                       2121
```

(2) INFORMATION FOR SEQ ID NO: 4:

(i) SEQUENCE CHARACTERISTICS:
        (A) LENGTH: 501 amino acids
        (B) TYPE: Amino Acid
        (D) TOPOLOGY: Linear (xi) SEQUENCE DESCRIPTION: SEQ ID NO: 4:

```
Met Ala Ala Ser Val Thr Ser Pro Gly Ser Leu Glu Leu Leu
 1               5                  10                  15

Gln Pro Gly Phe Ser Lys Thr Leu Leu Gly Thr Arg Leu Glu Ala
                20                  25                  30

Lys Tyr Leu Cys Ser Ala Cys Lys Asn Ile Leu Arg Arg Pro Phe
                35                  40                  45

Gln Ala Gln Cys Gly His Arg Tyr Cys Ser Phe Cys Leu Thr Ser
                50                  55                  60

Ile Leu Ser Ser Gly Pro Gln Asn Cys Ala Ala Cys Val Tyr Glu
                65                  70                  75

Gly Leu Tyr Glu Glu Gly Ile Ser Ile Leu Glu Ser Ser Ser Ala
                80                  85                  90

Phe Pro Asp Asn Ala Ala Arg Arg Glu Val Glu Ser Leu Pro Ala
                95                 100                 105

Val Cys Pro Asn Asp Gly Cys Thr Trp Lys Gly Thr Leu Lys Glu
               110                 115                 120

Tyr Glu Ser Cys His Glu Gly Leu Cys Pro Phe Leu Leu Thr Glu
               125                 130                 135

Cys Pro Ala Cys Lys Gly Leu Val Arg Leu Ser Glu Lys Glu His
               140                 145                 150

His Thr Glu Gln Glu Cys Pro Lys Arg Ser Leu Ser Cys Gln His
               155                 160                 165

Cys Arg Ala Pro Cys Ser His Val Asp Leu Glu Val His Tyr Glu
               170                 175                 180

Val Cys Pro Lys Phe Pro Leu Thr Cys Asp Gly Cys Gly Lys Lys
               185                 190                 195

Lys Ile Pro Arg Glu Thr Phe Gln Asp His Val Arg Ala Cys Ser
               200                 205                 210

Lys Cys Arg Val Leu Cys Arg Phe His Thr Val Gly Cys Ser Glu
               215                 220                 225

Met Val Glu Thr Glu Asn Leu Gln Asp His Glu Leu Gln Arg Leu
               230                 235                 240

Arg Glu His Leu Ala Leu Leu Leu Ser Ser Phe Leu Glu Ala Gln
               245                 250                 255

Ala Ser Pro Gly Thr Leu Asn Gln Val Gly Pro Glu Leu Leu Gln
               260                 265                 270

Arg Cys Gln Ile Leu Glu Gln Lys Ile Ala Thr Phe Glu Asn Ile
               275                 280                 285

Val Cys Val Leu Asn Arg Glu Val Glu Arg Val Ala Val Thr Ala
               290                 295                 300

Glu Ala Cys Ser Arg Gln His Arg Leu Asp Gln Asp Lys Ile Glu
               305                 310                 315
```

```
Ala Leu Ser Asn Lys Val Gln Gln Leu Glu Arg Ser Ile Gly Leu
            320                 325                 330

Lys Asp Leu Ala Met Ala Asp Leu Glu Gln Lys Val Ser Glu Leu
            335                 340                 345

Glu Val Ser Thr Tyr Asp Gly Val Phe Ile Trp Lys Ile Ser Asp
            350                 355                 360

Phe Thr Arg Lys Arg Gln Glu Ala Val Ala Gly Arg Thr Pro Ala
            365                 370                 375

Ile Phe Ser Pro Ala Phe Tyr Thr Ser Arg Tyr Gly Tyr Lys Met
            380                 385                 390

Cys Leu Arg Val Tyr Leu Asn Gly Asp Gly Thr Gly Arg Gly Thr
            395                 400                 405

His Leu Ser Leu Phe Phe Val Val Met Lys Gly Pro Asn Asp Ala
            410                 415                 420

Leu Leu Gln Trp Pro Phe Asn Gln Lys Val Thr Leu Met Leu Leu
            425                 430                 435

Asp His Asn Asn Arg Glu His Val Ile Asp Ala Phe Arg Pro Asp
            440                 445                 450

Val Thr Ser Ser Ser Phe Gln Arg Pro Val Ser Asp Met Asn Ile
            455                 460                 465

Ala Ser Gly Cys Pro Leu Phe Cys Pro Val Ser Lys Met Glu Ala
            470                 475                 480

Lys Asn Ser Tyr Val Arg Asp Asp Ala Ile Phe Ile Lys Ala Ile
            485                 490                 495

Val Asp Leu Thr Gly Leu
            500

(2) INFORMATION FOR SEQ ID NO: 5:

(i) SEQUENCE CHARACTERISTICS:
        (A) LENGTH: 44 amino acids
        (B) TYPE: Amino Acid
        (D) TOPOLOGY: Linear (xi) SEQUENCE DESCRIPTION: SEQ ID NO: 5:

Asp Leu Leu Cys Pro Ile Cys Met Gln Ile Ile Lys Asp Ala Phe
 1               5                  10                  15

Leu Thr Ala Cys Gly His Ser Phe Cys Tyr Met Cys Ile Ile Thr
                20                  25                  30

His Leu Arg Asn Lys Ser Asp Cys Pro Cys Cys Ser Gln His
                35                  40

(2) INFORMATION FOR SEQ ID NO: 6:

(i) SEQUENCE CHARACTERISTICS:
        (A) LENGTH: 47 amino acids
        (B) TYPE: Amino Acid
        (D) TOPOLOGY: Linear (xi) SEQUENCE DESCRIPTION: SEQ ID NO: 6:

Glu Leu Ser Cys Ser Ile Cys Leu Glu Pro Phe Lys Glu Pro Val
 1               5                  10                  15

Thr Thr Pro Cys Gly His Asn Phe Cys Gly Ser Cys Leu Asn Glu
                20                  25                  30

Thr Trp Ala Val Gln Gly Ser Pro Tyr Leu Cys Pro Gln Cys Arg
                35                  40                  45

Ala Val
```

(2) INFORMATION FOR SEQ ID NO: 7:

(i) SEQUENCE CHARACTERISTICS:
        (A) LENGTH: 44 amino acids
        (B) TYPE: Amino Acid
        (D) TOPOLOGY: Linear (xi) SEQUENCE DESCRIPTION: SEQ ID NO: 7:

```
Leu Leu Arg Cys His Ile Cys Lys Asp Phe Leu Lys Val Pro Val
 1               5                  10                  15
Leu Thr Pro Cys Gly His Thr Phe Cys Ser Leu Cys Ile Arg Thr
                20                  25                  30
His Leu Asn Asn Gln Pro Asn Cys Pro Leu Cys Leu Phe Glu
                35                  40
```

(2) INFORMATION FOR SEQ ID NO: 8:

(i) SEQUENCE CHARACTERISTICS:
        (A) LENGTH: 44 amino acids
        (B) TYPE: Amino Acid
        (D) TOPOLOGY: Linear (xi) SEQUENCE DESCRIPTION: SEQ ID NO: 8:

```
Ala Phe Arg Cys His Val Cys Lys Asp Phe Tyr Asp Ser Pro Met
 1               5                  10                  15
Leu Thr Ser Cys Asn His Thr Phe Cys Ser Leu Cys Ile Arg Arg
                20                  25                  30
Cys Leu Ser Val Asp Ser Lys Cys Pro Leu Cys Arg Ala Thr
                35                  40
```

(2) INFORMATION FOR SEQ ID NO: 9:

(i) SEQUENCE CHARACTERISTICS:
        (A) LENGTH: 45 amino acids
        (B) TYPE: Amino Acid
        (D) TOPOLOGY: Linear (xi) SEQUENCE DESCRIPTION: SEQ ID NO: 9:

```
Ser Ile Ser Cys Gln Ile Cys Glu His Ile Leu Ala Asp Pro Val
 1               5                  10                  15
Glu Thr Asn Cys Lys His Val Phe Cys Arg Val Cys Ile Leu Arg
                20                  25                  30
Cys Leu Lys Val Met Gly Ser Tyr Cys Pro Ser Cys Arg Tyr Pro
                35                  40                  45
```

(2) INFORMATION FOR SEQ ID NO: 10:

(i) SEQUENCE CHARACTERISTICS:
        (A) LENGTH: 45 amino acids
        (B) TYPE: Amino Acid
        (D) TOPOLOGY: Linear (xi) SEQUENCE DESCRIPTION: SEQ ID NO: 10:

```
Glu Val Thr Cys Pro Ile Cys Leu Asp Pro Phe Val Glu Pro Val
 1               5                  10                  15
Ser Ile Glu Cys Gly His Ser Phe Cys Gln Glu Cys Ile Ser Gln
                20                  25                  30
Val Gly Lys Gly Gly Gly Ser Val Cys Ala Val Cys Arg Gln Arg
                35                  40                  45
```

(2) INFORMATION FOR SEQ ID NO: 11:

```
       (i) SEQUENCE CHARACTERISTICS:
            (A) LENGTH: 46 amino acids
            (B) TYPE: Amino Acid
            (D) TOPOLOGY: Linear (xi) SEQUENCE DESCRIPTION: SEQ ID NO: 11:

Glu Leu Met Cys Pro Ile Cys Leu Asp Met Leu Lys Asn Thr Met
 1               5                  10                  15

Thr Thr Lys Glu Cys Leu His Arg Phe Cys Ser Asp Cys Ile Val
                20                  25                  30

Thr Ala Leu Arg Ser Gly Asn Lys Glu Cys Pro Thr Cys Arg Lys
                35                  40                  45

Lys (2) INFORMATION FOR SEQ ID NO: 12:

(i) SEQUENCE CHARACTERISTICS:
            (A) LENGTH: 50 amino acids
            (B) TYPE: Amino Acid
            (D) TOPOLOGY: Linear (xi) SEQUENCE DESCRIPTION: SEQ ID NO: 12:

Glu Val Thr Cys Pro Ile Cys Leu Glu Leu Leu Lys Glu Pro Val
 1               5                  10                  15

Ser Ala Asp Cys Asn His Ser Phe Cys Arg Ala Cys Ile Thr Leu
                20                  25                  30

Asn Tyr Glu Ser Asn Arg Asn Thr Asp Gly Lys Gly Asn Cys Pro
                35                  40                  45

Val Cys Arg Val Pro
                50

(2) INFORMATION FOR SEQ ID NO: 13:

(i) SEQUENCE CHARACTERISTICS:
            (A) LENGTH: 47 amino acids
            (B) TYPE: Amino Acid
            (D) TOPOLOGY: Linear (xi) SEQUENCE DESCRIPTION: SEQ ID NO: 13:

Glu Thr Thr Cys Pro Val Cys Leu Gln Tyr Phe Ala Glu Pro Met
 1               5                  10                  15

Met Leu Asp Cys Gly His Asn Ile Cys Cys Ala Cys Leu Ala Arg
                20                  25                  30

Cys Trp Gly Thr Ala Glu Thr Asn Val Ser Cys Pro Gln Cys Arg
                35                  40                  45

Glu Thr (2) INFORMATION FOR SEQ ID NO: 14:

(i) SEQUENCE CHARACTERISTICS:
            (A) LENGTH: 48 amino acids
            (B) TYPE: Amino Acid
            (D) TOPOLOGY: Linear (xi) SEQUENCE DESCRIPTION: SEQ ID NO: 14:

Phe Gln Leu Cys Lys Ile Cys Ala Glu Asn Asp Lys Asp Val Lys
 1               5                  10                  15

Ile Glu Pro Cys Gly His Leu Met Cys Thr Ser Cys Leu Thr Ser
                20                  25                  30

Trp Gln Glu Ser Glu Gly Gln Gly Ser Ser Gly Cys Pro Phe Cys
```

```
                35                  40                  45
Arg Cys Glu (2) INFORMATION FOR SEQ ID NO: 15:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO: 15:

Gly Gly Phe Lys Leu Val Thr Cys Asp Phe Cys Lys Arg Asp Asp
1               5                   10                  15

Ile Lys Lys Lys Glu Leu Glu Thr His Tyr Lys Thr Cys
                20                  25

(2) INFORMATION FOR SEQ ID NO: 16:

(i) SEQUENCE CHARACTERISTICS:
        (A) LENGTH: 26 amino acids
        (B) TYPE: Amino Acid
        (D) TOPOLOGY: Linear (xi) SEQUENCE DESCRIPTION: SEQ ID NO: 16:

Gln Asp Leu Ala Val Cys Asp Val Cys Asn Arg Lys Phe Arg His
1               5                   10                  15

Lys Asp Tyr Leu Arg Asp His Gln Lys Thr His
                20                  25

(2) INFORMATION FOR SEQ ID NO: 17:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO: 17:

Thr Gly Lys Tyr Pro Phe Ile Cys Ser Glu Cys Gly Lys Ser Phe
1               5                   10                  15

Met Asp Lys Arg Tyr Leu Lys Ile His Ser Asn Val His
                20                  25

(2) INFORMATION FOR SEQ ID NO: 18:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO: 18:

Thr Gly Glu Lys Pro Tyr Thr Cys Thr Val Cys Gly Lys Lys Phe
1               5                   10                  15

Ile Asp Arg Ser Ser Val Val Lys His Ser Arg Thr His
                20                  25

(2) INFORMATION FOR SEQ ID NO: 19:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO: 19:

Arg Lys Lys Phe Pro His Ile Cys Gly Glu Cys Gly Lys Gly Phe
```

```
                  1               5                  10                 15
Arg His Pro Ser Ala Leu Lys Lys His Ile Arg Val His
                 20                 25

(2) INFORMATION FOR SEQ ID NO: 20:

(i) SEQUENCE CHARACTERISTICS:
          (A) LENGTH: 28 amino acids
          (B) TYPE: Amino Acid
          (D) TOPOLOGY: Linear (xi) SEQUENCE DESCRIPTION: SEQ ID NO: 20:

Ser Glu Glu Lys Pro Phe Glu Cys Glu Glu Cys Gly Lys Lys Phe
  1               5                  10                 15
Arg Thr Ala Arg His Leu Val Lys His Gln Arg Ile His
                 20                 25

(2) INFORMATION FOR SEQ ID NO: 21:

(i) SEQUENCE CHARACTERISTICS:
          (A) LENGTH: 28 amino acids
          (B) TYPE: Amino Acid
          (D) TOPOLOGY: Linear (xi) SEQUENCE DESCRIPTION: SEQ ID NO: 21:

Pro Asn Glu Gln Met Ala Gln Cys Pro Ile Cys Gln Gln Phe Tyr
  1               5                  10                 15
Pro Leu Lys Ala Leu Glu Lys Thr His Leu Asp Glu Cys
                 20                 25

(2) INFORMATION FOR SEQ ID NO: 22:

(i) SEQUENCE CHARACTERISTICS:
          (A) LENGTH: 28 amino acids
          (B) TYPE: Amino Acid
          (D) TOPOLOGY: Linear (xi) SEQUENCE DESCRIPTION: SEQ ID NO: 22:

Pro Asp Asp Gly Leu Val Ala Cys Pro Ile Cys Leu Thr Arg Met
  1               5                  10                 15
Lys Glu Gln Gln Val Asp Arg His Leu Asp Thr Ser Cys
                 20                 25

(2) INFORMATION FOR SEQ ID NO: 23:

(i) SEQUENCE CHARACTERISTICS:
          (A) LENGTH: 21 base pairs
          (B) TYPE: Nucleic Acid
          (C) STRANDEDNESS: Single
          (D) TOPOLOGY: Linear (xi) SEQUENCE DESCRIPTION: SEQ ID NO: 23:

CCTTGTGCCT GCAGAGAGAA G                                                 21

(2) INFORMATION FOR SEQ ID NO: 24:

(i) SEQUENCE CHARACTERISTICS:
          (A) LENGTH: 35 base pairs
          (B) TYPE: Nucleic Acid
          (C) STRANDEDNESS: Single
          (D) TOPOLOGY: Linear (xi) SEQUENCE DESCRIPTION: SEQ ID NO: 24:

CTAGGTTAAC TTTCGGTGCT CCCCAGCAGG GTCTC                                  35
```

(2) INFORMATION FOR SEQ ID NO: 25:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 25:

CTAGGTTAAC TGGAGAAGGG GACCTGCTCG TCCTT                35

(2) INFORMATION FOR SEQ ID NO: 26:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 26:

CTAGGTTAAC TGCTGGCTTG GGAGGAGCAC TGTGA                35

(2) INFORMATION FOR SEQ ID NO: 27:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 27:

CTAGGTTAAC TGCTCCCGGT GCTGGCCCGG GCCTC                35

(2) INFORMATION FOR SEQ ID NO: 28:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO: 28:

CTAGGTTAAC TGCACTGGCC GAGCTCTCCA GGGA                 34

(2) INFORMATION FOR SEQ ID NO: 29:

(i) SEQUENCE CHARACTERISTICS:
        (A) LENGTH: 15 base pairs
        (B) TYPE: Nucleic Acid
        (C) STRANDEDNESS: Single
        (D) TOPOLOGY: Linear (xi) SEQUENCE DESCRIPTION: SEQ ID NO: 29:

GTGATGAGAA TTCAT                                          15

(2) INFORMATION FOR SEQ ID NO: 30:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 30:

CGATGAATTC TCATCACTGC A                              21

(2) INFORMATION FOR SEQ ID NO: 31:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 31:

```
GATCGGATCC AAAAGAAGC CCTTGTGCCT GCA                                33
```

(2) INFORMATION FOR SEQ ID NO: 32:

(i) SEQUENCE CHARACTERISTICS:
        (A) LENGTH: 16 base pairs
        (B) TYPE: Nucleic Acid
        (C) STRANDEDNESS: Single
        (D) TOPOLOGY: Linear (xi) SEQUENCE DESCRIPTION: SEQ ID NO: 32:

```
GCCTGGTTAA CTGGGC                                                  16
```

(2) INFORMATION FOR SEQ ID NO: 33:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO: 33:

```
GCNCCNATGG CNYTNGARC                                               19
```

(2) INFORMATION FOR SEQ ID NO: 34:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO: 34:

```
GCNCCNATGG CNYTNGARA                                               19
```

(2) INFORMATION FOR SEQ ID NO: 35:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO: 35:

```
GCNCCNATGG CNYTNGARG                                               19
```

(2) INFORMATION FOR SEQ ID NO: 36:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO: 36:

```
GYTCNARNGC CATNGGNGC                                               19
```

(2) INFORMATION FOR SEQ ID NO: 37:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO: 37:

TYTCNARNGC CATNGGNGC                                                19

(2) INFORMATION FOR SEQ ID NO: 38:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO: 38:

CYTCNARNGC CATNGGNGC                                                19

(2) INFORMATION FOR SEQ ID NO: 39:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO: 39:

AARCAYGCNT AYGTNAA                                                  17

(2) INFORMATION FOR SEQ ID NO: 40:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO: 40:

TTNACRTANG CRTGYTT                                                  17

(2) INFORMATION FOR SEQ ID NO: 41:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 41:

Ala Pro Met Ala Leu Glu Arg
 1               5

(2) INFORMATION FOR SEQ ID NO: 42:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO: 42:

Lys His Ala Tyr Val Lys
 1               5

(2) INFORMATION FOR SEQ ID NO: 43:

(i) SEQUENCE CHARACTERISTICS:
            (A) LENGTH: 7 amino acids
            (B) TYPE: Amino Acid
            (D) TOPOLOGY: Linear (xi) SEQUENCE DESCRIPTION: SEQ ID NO: 43:

Pro Gly Ser Asn Leu Gly Ser
 1               5

(2) INFORMATION FOR SEQ ID NO: 44:

(i) SEQUENCE CHARACTERISTICS:
            (A) LENGTH: 8 amino acids
            (B) TYPE: Amino Acid
            (D) TOPOLOGY: Linear (xi) SEQUENCE DESCRIPTION: SEQ ID NO: 44:

Lys Asp Asp Thr Met Phe Leu Lys
 1               5

(2) INFORMATION FOR SEQ ID NO: 45:

(i) SEQUENCE CHARACTERISTICS:
            (A) LENGTH: 37 base pairs
            (B) TYPE: Nucleic Acid
            (C) STRANDEDNESS: Single
            (D) TOPOLOGY: Linear (xi) SEQUENCE DESCRIPTION: SEQ ID NO: 45:

TCGATCGTCG ACCAAAAAGA AGCCCTCCTG CCTACAA                                37

(2) INFORMATION FOR SEQ ID NO: 46:

(i) SEQUENCE CHARACTERISTICS:
            (A) LENGTH: 28 base pairs
            (B) TYPE: Nucleic Acid
            (C) STRANDEDNESS: Single
            (D) TOPOLOGY: Linear (xi) SEQUENCE DESCRIPTION: SEQ ID NO: 46:

CTAGAGATCT CAGGGGTCAG GCCACTTT                                         28

(2) INFORMATION FOR SEQ ID NO: 47:

(i) SEQUENCE CHARACTERISTICS:
            (A) LENGTH: 41 base pairs
            (B) TYPE: Nucleic Acid
            (C) STRANDEDNESS: Single
            (D) TOPOLOGY: Linear (xi) SEQUENCE DESCRIPTION: SEQ ID NO: 47:

CTAGAGATCT GTTAACTTTC GGTGCTCCCC AGCAGGGTCT C                          41

(2) INFORMATION FOR SEQ ID NO: 48:

(i) SEQUENCE CHARACTERISTICS:
            (A) LENGTH: 41 base pairs
            (B) TYPE: Nucleic Acid
            (C) STRANDEDNESS: Single
            (D) TOPOLOGY: Linear (xi) SEQUENCE DESCRIPTION: SEQ ID NO: 48:

CTAGAGATCT GTTAACTGGA GAAGGGGACC TGCTCGTCCT T                          41

(2) INFORMATION FOR SEQ ID NO: 49:

(i) SEQUENCE CHARACTERISTICS:

(A) LENGTH: 41 base pairs
        (B) TYPE: Nucleic Acid
        (C) STRANDEDNESS: Single
        (D) TOPOLOGY: Linear (xi) SEQUENCE DESCRIPTION: SEQ ID NO: 49:

CTAGAGATCT GTTAACTGCT GGCTTGGGAG GAGCACTGTG A                41

(2) INFORMATION FOR SEQ ID NO: 50:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO: 50:

TCGATCGTCG ACCGCCTCCA GCTCAGCCCC TGAT                        34

(2) INFORMATION FOR SEQ ID NO: 51:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 51:

GATCGGATCC GGAGACACAG ATTCCAGCCC C                           31

(2) INFORMATION FOR SEQ ID NO: 52:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 52:

GATCGAATTC TTAACTCTTC GGTGCTCCCC AGCAG                       35

(2) INFORMATION FOR SEQ ID NO: 53:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 53:

GATCGGATCC TTGTGGTGTG TGGGGGTTGT                             30

(2) INFORMATION FOR SEQ ID NO: 54:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO: 54:

CCTGGCTGGC CTAATGT                                           17

(2) INFORMATION FOR SEQ ID NO: 55:

(i) SEQUENCE CHARACTERISTICS:
        (A) LENGTH: 60 base pairs

```
        (B) TYPE: Nucleic Acid
        (C) STRANDEDNESS: Single
        (D) TOPOLOGY: Linear (xi) SEQUENCE DESCRIPTION: SEQ ID NO: 55:

GATCGACTCG AGATGCCCAA GAAGAAGCGG AAGGTGGCTG CAGCCAGTGT            50

GACTTCCCCT                                                       60

(2) INFORMATION FOR SEQ ID NO: 56:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO: 56:

CTCTGGCGAA GAAGTCC                                               17

(2) INFORMATION FOR SEQ ID NO: 57:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 57:

GATCGGATCC GCCTCCAGCT CAGCCCCTGA T                               31

(2) INFORMATION FOR SEQ ID NO: 58:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 58:

GATCGGATCC AGCCAGCAGC TTCTCCTTCA C                               31

(2) INFORMATION FOR SEQ ID NO: 59:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 59:

GATCGGATCC GCTCAGGCTC TTTTGGGGCA                                 30
```

ANTIBODIES TO TUMOR NECROSIS FACTOR RECEPTOR ASSOCIATED FACTOR POLYPEPTIDES

RELATED APPLICATIONS

This application is a continuation application of Ser. No. 10/283,500, filed Oct. 30, 2002, which is a continuation application of Ser. No. 08/779,599, filed Jan. 7, 1997, now issued as U.S. Pat. No. 6,500,922 on Dec. 31, 2002, which is a continuation application of Ser. No. 08/744,139, filed Nov. 5, 1996, now issued as U.S. Pat. No. 5,869,612 on Feb. 9, 1999, which is a continuation application of Ser. No. 08/250,858, filed May 27, 1994, now issued as U.S. Pat. No. 5,708,142 on Jan. 13, 1998, the contents of which applications are expressly incorporated herein by reference.

FIELD OF THE INVENTION

The present invention concerns novel polypeptide factors. More particularly, the invention concerns factors associated with the type 2 tumor necrosis factor receptor (TNF-R2).

BACKGROUND OF THE INVENTION

Tumor necrosis factor (TNF, also referred to as TNF-α) is a potent cytokine produced mainly by activated macrophages and a few other cell types. The large number of biological effects elicited by TNF include hemorrhagic necrosis of transplanted tumors, cytotoxicity, a role in endotoxin shock, inflammatory, immunoregulatory, proliferative, and antiviral responses [reviewed in Goeddel, D. V. et al., *Cold Spring Harbor Symposia on Quantitative Biology* 51, 597-609 (1986); Beutler, B. and Cerami, A., *Ann. Rev. Biochem.* 57, 505-518 (1988); Old, L. J., *Sci. Am.* 258 (5), 59-75 (1988); Fiers, W. *FEBS Lett.* 285 (2), 199-212 (1991)]. The literature has reported that TNF and other cytokines such as IL-1 may protect against the deleterious effects of ionizing radiation produced during the course of radiotherapy, such as denaturation of enzymes, lipid peroxidation, and DNA damage [(Neta et al., *J. Immunol.* 136 (7): 2483, (1987); Neta et al., *Fed. Proc.* 46: 1200 (abstract), (1987); Urbaschek et al., *Lymphokine Res.* 6: 179 (1987); U.S. Pat. No. 4,861,587; Neta et al., *J. Immunol.* 140: 108 (1988)]. A related molecule, lymphotoxin (LT, also referred to as TNF-β), that is produced by activated lymphocytes shows a similar but not identical spectrum of biological activities as TNF (see, e.g. Goeddel, D. V. et al., supra, and Fiers, W., supra). TNF was described by Pennica et al., *Nature* 312, 721 (1984); LT was described by Gray et al., *Nature* 312, 724 (1984).

The first step in the induction of the various cellular responses mediated by TNF or LT is their binding to specific cell surface receptors. Two distinct TNF receptors of approximately 55-kDa (TNF-R1) and 75-kDa (TNF-R2) have been identified [Hohmann, H. P. et al., *J. Biol. Chem.* 264, 14927-14934 (1989); Brockhaus, M. et al., *Proc. Natl. Acad. Sci. USA* 87, 3127-3131 (1990)], and human and mouse cDNAs corresponding to both receptor types have been isolated and characterized [Loetscher, H. et al., *Cell* 61, 351 (1990); Schall, T. J. et al., *Cell* 61, 361 (1990); Smith, C. A. et al., *Science* 248, 1019 (1990); Lewis, M. et al., *Proc. Natl. Acad. Sci. USA* 88, 2830-2834 (1991); Goodwin, R. G. et al., *Mol. Cell. Biol.* 11, 3020-3026 (1991)]. Both TNF-Rs share the typical structure of cell surface receptors including extracellular, transmembrane and intracellular regions. The extracellular portions of both receptors are found naturally also as soluble TNF-binding proteins [Nophar, Y. et al., *EMBO J.* 9, 3269 (1990); and Kohno, T. et al., *Proc. Natl. Acad. Sci. U.S.A.* 87, 8331 (1990)]]. The amino acid sequence of human TNF-R1 and the underlying nucleotide sequence are disclosed in EP 417,563 (published 20 Mar. 1991), whereas EP 418,014 (published 20 Mar. 1991) discloses the amino acid and nucleotide sequences of human TNF-R2.

Although not yet systematically investigated, the majority of cell types and tissues appear to express both TNF receptors.

The individual roles of the two TNF receptors, and particularly those of TNF-R2, in cell signaling are far from entirely understood, although studies performed by poly- and monoclonal antibodies (mAbs) that are specific for either TNF-R1 or TNF-R2 have provided some very valuable insight into the functions and interactions of these receptors.

It has been observed that both polyclonal and monoclonal antibodies directed against TNF-R1 can act as specific agonists for this receptor and elicit several TNF activities such as cytotoxicity, fibroblast proliferation, resistance to chlamydiae, and synthesis of prostaglandin $E_2$ [Engelmann, H. et al., *J. Biol. Chem.* 265, 14497-14504 (1990); Espevik, T. et al., *J. Exp. Med.* 171, 415-426 (1990); Shalaby, M. R. et al., *J. Exp. Med.* 172, 1517-1520 (1990)]. Agonist antibodies to TNF-R1 with antiviral activity are disclosed in copending application Ser. No. 07/856,989 filed 24 Mar. 1992.

In addition, polyclonal antibodies to both murine TNF-R1 and TNF-R2 have been developed, have been shown to behave as specific receptor agonists and induce a subset of murine TNF activities. While the murine TNF-R1 was shown to be responsible for signaling cytotoxicity and the induction of several genes, the murine TNF-R2 was shown to be capable of signaling proliferation of primary thymocytes and a cytotoxic T cell line, CT6 [Tartaglia, L. A. et al., *Proc. Natl. Acad. Sci. USA* 88, 9292-9296 (1991)]. The ability of TNF-R2 to stimulate human thymocyte proliferation has been demonstrated in experiments with monoclonal antibodies directed against the human receptor.

Monoclonal antibodies against human TNF-R1 that block the binding of TNF to TNF-R1 and antagonize several of the TNF effects have also been described [Espevik, T. et al., Supra; Shalaby, M. R. et al., Supra; Naume, B. et al., *J. Immunol.* 146, 3035-3048 (1991)].

In addition, several reports described monoclonal antibodies directed against TNF-R2 that can partially antagonize the same TNF responses (such as cytotoxicity and activation of NF-κB) that are induced by TNF-R1 agonists [Shalaby, M. R. et al., Supra; Naume, B. et al., Supra; and Hohmann, H. P. et al., *J. Biol. Chem.* 265, 22409-22417 (1990)].

It is now well established that although the two human TNF receptors are both active in signal transduction, they are able to mediate distinct cellular responses. While TNF-R1 appears to be responsible for signaling most TNF responses, the thymocyte proliferation stimulating activity of TNF is specifically mediated by TNF-R2. In addition, TNF-R2 activates the transcription factor NF-κB (Lenardo & Baltimore, *Cell* 58: 227-229 [1989]) and mediates the transcriptional induction of the granulocyte-macrophage colony stimulating factor (GM-CSF) gene (Miyatake et al., *EMBO J.* 4: 2561-2568 [1985]; Stanley et al., *EMBO J.* 4: 2569-2573 [1985]) and the A20 zinc finger protein gene (Opipari et al., *J. Biol. Chem.* 265: 14705-14708 [1990]) in CT6 cells. TNF-R2 also participates as an accessory component to TNF-R1 in the signaling of responses primarily mediated by TNF-R1, like cytotoxicity ([Tartaglia, L. A. and Goeddel, D. V., *Immunol. Today* 13, 151-153 [1992]).

SUMMARY OF THE INVENTION

Although TNF itself, the TNF receptors and TNF activities mediated by the two receptors have been studied extensively, the post-receptor signal transduction mechanisms are unknown (see the review article by Beyaert, R. & Fiers, W., "Molecular mechanisms of tumor necrosis factor-induced cytotoxicity: what we do understand and what we do not", *FEBS Letters* 340, 9-16 (1994)). This is especially true for the very first step in the TNF receptor signal transduction cascade, i.e. for the question of how the membrane-bound receptor sends a signal into the cell after activation by the ligand, TNF.

The present invention is based on the hypothesis that polypeptide factors associated with the intracellular domain of TNF-R2 exist and participate in the TNF-R2 signal transduction cascade. More specifically, this invention is based on research directed to the identification and isolation of native polypeptide factors that are capable of association with the intracellular domain of TNF-R2 and participate in the intracellular post-receptor signaling of TNF biological activities.

It is known that the TNF induced proliferation of murine CT6 cells is mediated by TNF-R2 (Tartaglia et al., [1991], supra). To identify factors that are associated with the intracellular domain of hTNF-R2, the receptor was immunoprecipitated from lysates of [$^{35}$S]-labeled transfected CT6 cells and from unlabeled transfected human embryonic kidney 293 cells, which were then incubated with labeled lysate from untransfected CT6 cells. Several polypeptides with apparent molecular weights of 45-50 kD and one with an approximate molecular weight of 68 kD were specifically coprecipitated with the immunoprecipitated hTNF-R2. These are hereinafter collectively referred to as tumor necrosis factor receptor associated polypeptides, or TRAFs. Of the factors identified two have so far been purified and cloned. These two factors are designated as tumor necrosis factor receptor associated factors 1 and 2 (TRAF1 and TRAF2; SEQ. ID. NOs: 2 and 4). A comparison of the amino acid sequences of TRAF1 and TRAF2 revealed that they share a high degree of amino acid identity in their C-terminal domains (53% identity over 230 amino acids), while their N-terminal domains are unrelated. These new factors are believed to play a key role in the post-receptor signaling of TNF. Since the intracellular domain of TNF-R2 does not display any sequence homology to any other known receptor or protein, these signaling molecules might represent a novel signal transduction mechanism, the understanding of which can greatly contribute to the development of new strategies to improve the therapeutic value of TNF.

In one aspect, the present invention concerns a family of novel factors (TRAFs) capable of specific association with the intracellular domain of a native TNF-R2. The invention specifically concerns tumor necrosis factor receptor associated factors 1 and 2 (TRAF1 and TRAF2, SEQ. ID. NOs. 2 and 4), including the native factors from any human or non-human animal species and their functional derivatives.

In another aspect, the invention concerns an isolated nucleic acid molecule comprising a nucleotide sequence encoding a TRAF polypeptide.

In yet another aspect, the invention concerns an expression vector comprising the foregoing nucleic acid molecule operably linked to control sequences recognized by a host cell transformed with the vector.

In a further aspect, the invention concerns a host cell transformed with the foregoing expression vector.

In a still further aspect, the invention concerns molecules (including polypeptides, e.g. antibodies and TRAF analogs and fragments, peptides and small organic molecules) which disrupt the interaction of a TNF-R2 receptor associated factor and TNF-R2.

The invention specifically concerns antibodies, capable of specific binding to a native TRAF polypeptide, and hybridoma cell lines producing such antibodies.

In a different aspect, the invention concerns a method of using a nucleic acid molecule encoding a TRAF polypeptide as hereinabove defined, comprising expressing such nucleic acid molecule in a cultured host cell transformed with a vector comprising said nucleic acid molecule operably linked to control sequences recognized by the host cell transformed with the vector, and recovering the encoded polypeptide from the host cell.

The invention further concerns a method for producing a TRAF polypeptide as hereinabove defined, comprising inserting into the DNA of a cell containing nucleic acid encoding said polypeptide a transcription modulatory element in sufficient proximity and orientation to the nucleic acid molecule to influence the transcription thereof.

The invention also provides a method of determining the presence of a TRAF polypeptide, comprising hybridizing DNA encoding such polypeptide to a test sample nucleic acid and determining the presence of TRAF polypeptide DNA.

In a further aspect, the invention concerns an isolated nucleic acid molecule encoding a fusion of an intracellular domain sequence of a native TNF-R2 and the DNA-binding domain of a transcriptional activator.

In a still further aspect, the invention concerns an isolated nucleic acid molecule encoding a fusion of a TRAF to the activation domain of a transcriptional activator.

The invention further concerns hybrid (fusion) polypeptides encoded by the foregoing nucleic acids.

The invention also covers vectors comprising one or both of the nucleic acid molecules encoding the foregoing fusion proteins.

In a different aspect, the invention concerns an assay for identifying a factor capable of specific binding to the intracellular domain of a native TNF-R2, comprising (a) expressing, in a single host cell carrying a reporter gene, nucleic acid molecules encoding a polypeptide comprising a fusion of an intracellular domain sequence of a native TNF-R2 to the DNA-binding domain of a transcriptional activator, and a fusion of a candidate factor to the activation domain of a transcriptional activator; and (b) monitoring the binding of the candidate factor to the TNF-R2 intracellular domain sequence by detecting the molecule encoded by the reporter gene.

The invention further relates to an assay for identifying a factor capable of specific association with the intracellular domain of a native TNF-R2, comprising (a) expressing nucleic acid molecules encoding a polypeptide comprising a fusion of an intracellular domain sequence of a native TNF-R2 to the DNA-binding domain of a transcriptional activator, and a second polypeptide comprising a fusion of a candidate polypeptide factor to the activation domain of a transcriptional activator, in a single host cell transfected with nucleic acid encoding a polypeptide factor capable of specific binding to said TNF-R2, and with nucleic acid encoding a reporter gene; and (b) monitoring the association of said candidate factor with said TNF-R2 or with said polypeptide factor capable of specific binding to said TNF-R2 by detecting the polypeptide encoded by said reporter gene.

In a further aspect, the invention concerns an assay for identifying a molecule capable of disrupting the association of a TRAF with the intracellular domain of a native TNF-R2, comprising contacting a cell expressing 1. a fusion of an intracellular domain sequence of a native TNF-R2 to the DNA-binding domain of a transcriptional activator, 2. a fusion of a native TRAF polypeptide to the activation domain of said transcriptional activator, and 3. a reporter gene, with a candidate molecule, and monitoring the ability of said candidate molecule to disrupt the association of said TRAF and TNF-R2 intracellular domain sequence by detecting the molecule encoded by the reporter gene. The cell, just in the previous assays is preferably a yeast cell.

In addition to the "two-hybrid" format described above, the assay my be performed in any conventional binding/inhibitor assay format. For example, one binding partner (TNF-R2 or TRAF) may be immobilized, and contacted with the other binding partner equipped with a detectable label, such as a radioactive label, e.g. $^{32}P$ and the binding (association) of the two partners is detected in the presence of a candidate inhibitor. The design of a specific binding assay is well within the skill of a person skilled in the art.

In a different aspect, the invention concerns a method of amplifying a nucleic acid test sample comprising priming a nucleic acid polymerase reaction with nucleic acid encoding a TRAF polypeptide, as defined above.

In another aspect, the invention concerns a method for detecting a nucleic acid sequence coding for a polypeptide molecule which comprises all or part of a TRAF polypeptide or a related nucleic acid sequence, comprising contacting the nucleic acid sequence with a detectable marker which binds specifically to at least part of the nucleic acid sequence, and detecting the marker so bound.

In yet another aspect, the invention concerns a method for treating a pathological condition associated with a TNF biological activity mediated, fully or partially, by TNF-R2, comprising administering to a patient in need a therapeutically effective amount of a TRAF or a molecule capable of disrupting the interaction of a TRAF and TNF-R2.

6 µg of nuclear extract prepared from CT6 cells that had been stimulated for 20 min with a 1:500 dilution of anti-mTNF-R2 polyclonal antibodies or the respective preimmune serum were incubated with a radiolabeled double-stranded oligonucleotide containing either two wild-type (wt) or mutant (mt) NF-kB binding sites and analyzed for the induction of NF-kB DNA-binding activity by electrophoretic mobility shift assay (Schütze et al., Cell 71, 765-776 [1992]). Binding reactions were either performed without competitor oligonucleotides or in the presence of a 500 fold excess of unlabeled competitor oligonucleotides containing mutant NF-kB binding sites or a binding site for the transcription factor AP-1 (Angel, P. et al., Mol. Cell. Biol. 7: 2256-2266 [1987]). F and B refer to free oligonucleotide probe and oligonucleotide probe in a complex with protein, respectively.

FIG. 2A-2B. Immunoprecipitation of hTNF-R2.

(A) $^{35}S$-labeled CT6 cells or CT6 cells expressing the hTNF-R2 were stimulated for 10 min with 100 ng/ml hTNF or left untreated. The cells were lysed and the hTNF-R2 immunoprecipitated as described in the text and analyzed by SDS-PAGE and autoradiography. The asterisk marks the band corresponding to the 75-80 kd hTNF-R2.

(B) The hTNF-R2 was immunoprecipitated from unstimulated or TNF-stimulated 293 or 293/TNF-R2 cells and incubated with lysates from $^{35}S$-labeled CT6 cells. Arrows indicate bands of 45-50 kd and 68 kd that coprecipitate specifically with the hTNF-R2 in both experiments. Molecular weight markers are indicated on the right in kd.

FIG. 3. Purification of GST-hTNF-R2icd fusion protein.

Glutathione-S-transferase (GST) and GST-hTNF-R2icd fusion protein were expressed in E. coli, purified as described in the text and analyzed by SDS-PAGE and Coomassie staining. Molecular weight markers are indicated on the right in kd.

Figure 4:
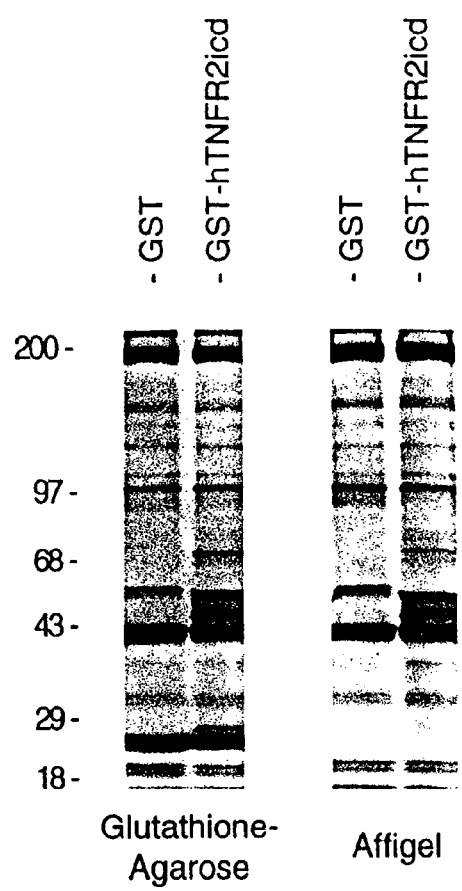

FIG. 4. Coprecipitation of GST-hTNF-R2icd fusion protein in CT6 cell extracts.

GST and GST-hTNF-R2icd fusion protein beads were incubated with lysates from $^{35}S$-labeled CT6 cells as described in the text and analyzed by SDS-PAGE and autoradiography. Arrows indicate bands of 45-50 kd and 68 kd that coprecipitate specifically with the GST-hTNF-R2icd fusion protein. Molecular weight markers are indicated on the right in kd.

Figure 5:
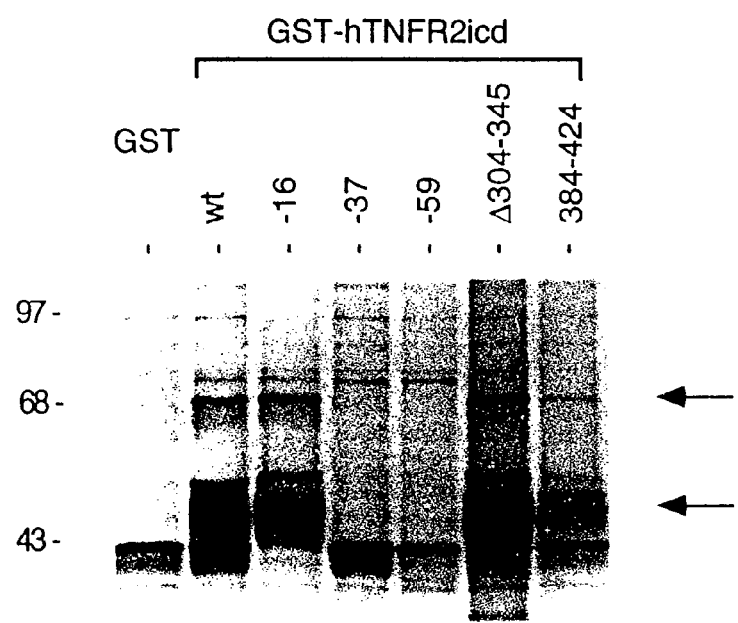

FIG. 5. Coprecipitation of GST-mutant hTNF-R2icd fusion proteins in CT6 cell extracts.

GST and GST-fusion proteins containing mutant intracellular domains of the hTNF-R2 were coupled to glutathione-agarose beads, incubated with lysates from $^{35}S$-labeled CT6 cells and analyzed by SDS-PAGE and autoradiography. Arrows indicate bands of 45-50 kd and 68 kd that coprecipitate specifically with the GST-fusion proteins containing the wild type (wt), the mutant −16, the Δ304-345 and the 384-424 intracellular domains of hTNF-R2 but are not associated with the mutant −37 and −59 intracellular domains. Note that the pattern of these bands is compressed in some cases due to the unlabeled fusion proteins migrating at the same size. Molecular weight markers are indicated on the right in kd.

FIG. 6A-6B. Competition of TNF-R2 associated factors with GST-hTNF-R2icd fusion proteins.

(A) The hTNF-R2 was immunoprecipitated from 293 and 293/TNF-R2 cells and incubated with lysates from $^{35}S$-labeled CT6 cells that had been preincubated with 50 µl of the indicated GST-hTNF-R2icd fusion protein beads as competitor. Reactions were analyzed by SDS-PAGE and autoradiography. Arrows indicate bands of 45-50 kd and 68 kd that coprecipitate specifically with the hTNF-R2 and that are depleted by preincubation with GST-fusion proteins containing the wild type (wt) and the mutant −16 intracellular domains of hTNF-R2 but not by preincubation with the mutant −37 and −59 intracellular domain fusion proteins.

(B) The 68 kd region of a similar experiment as described in (A) is shown. Molecular weight markers are indicated on the right in kd.

FIG. 7. Coprecipitation of GST-hTNF-R2icd fusion protein in Jurkat cell extracts.

GST and GST-hTNF-R2icd fusion protein beads were incubated with lysates from $^{35}S$-labeled Jurkat cells that had been stimulated for 10 min with 100 ng/ml hTNF or left untreated. Reactions were analyzed by SDS-PAGE and autoradiography. Arrows indicate bands of 45-50 kd, 67 kd and 73-75 kd that coprecipitate specifically with the GST-hTNF-R2icd fusion protein. Molecular weight markers are indicated on the right in kd.

Figure 8:
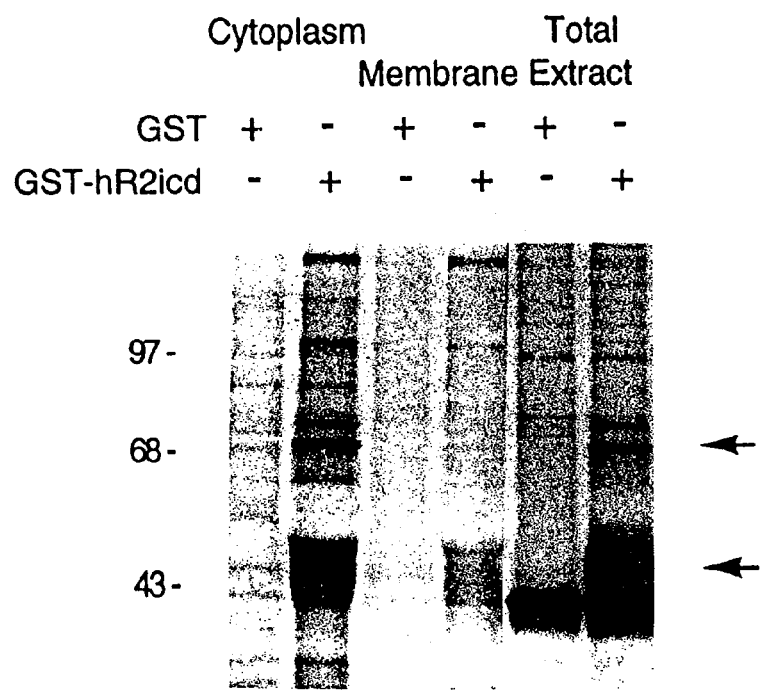

FIG. 8. Subcellular localization of TNF-R2 associated factors.

Cytoplasmic and cell membrane fractions were prepared from $^{35}$S-labeled CT6 cells as described in the text. These fractions and a detergent (total) extract form CT6 cells were incubated with GST and GST-hTNF-R2icd fusion beads, and the reactions analyzed by SDS-Page and autoradiography. Arrows indicate bands of 45-50 kd and 68 kd that coprecipitate specifically with the GST-hTNF-R2icd fusion protein. Molecular weight markers are indicated on the right in kd.

Figure 9:
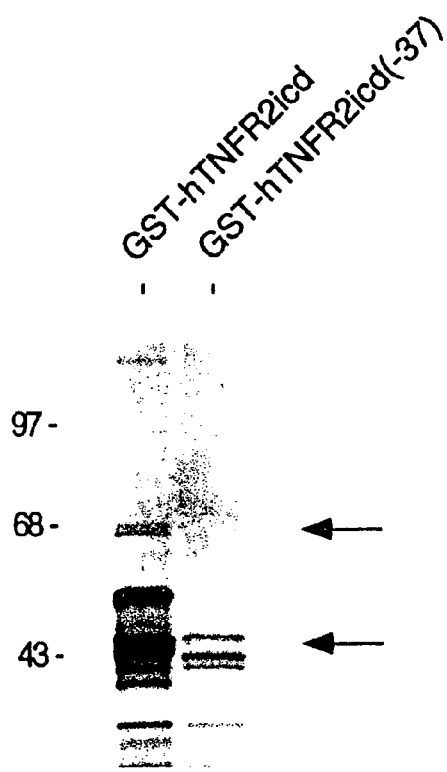

FIG. 9. Purification of TNF-R2 associated factors.

Large scale purification of TNF-R2 associated factors from CT6 cells by GST-hTNF-R2icd fusion protein affinity chromatography was performed as described in the text. One tenth of the obtained material was analyzed by SDS-PAGE and silver staining. Arrows indicate bands of 45-50 kd and 68-70 kd that were eluted specifically from the GST-hTNF-R2icd fusion protein affinity column. Molecular weight markers are indicated on the right in kd.

Figure 10A:
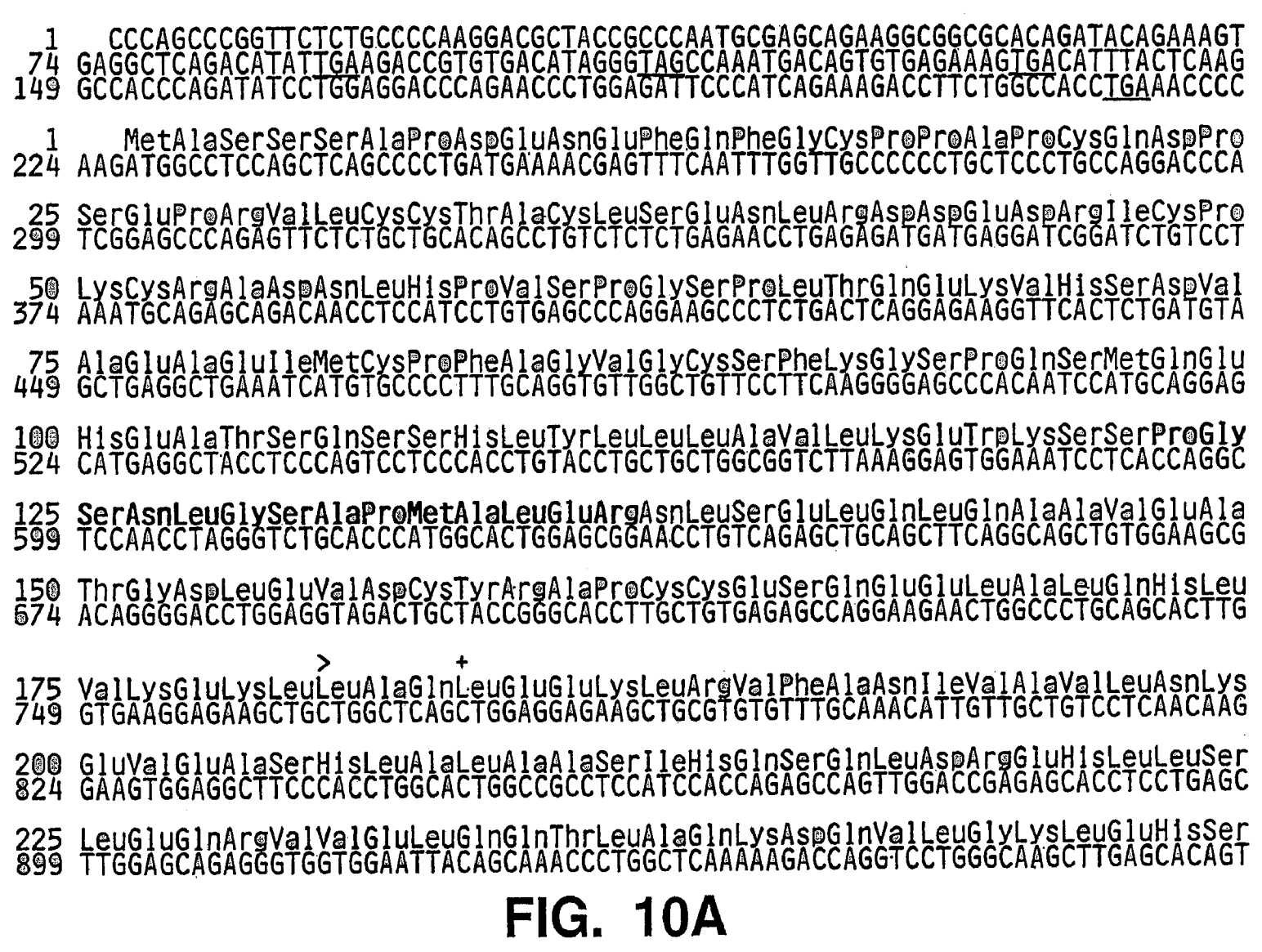

FIG. 10A-10B. Nucleotide and predicted amino acid sequence of the TRAF1 cDNA (SEQ. ID. NOS: 1 and 2).

The nucleic acid sequence of the TRAF1 cDNA is shown with numbering starting from the first base after the SalI cloning linker. The deduced protein sequence is displayed above with numbering from the initiation methionine. In-frame stop codons upstream of the initiation methionine are underlined. Amino acids identified by sequencing the purified TRAF1 protein are indicated in bold. The TRAF domain (see text) comprises amino acids 180 (>)-409 (<). The potential leucine zipper region (see text) extends between amino acids 183 (+)-259 (−). Amino acids within this region defining the heptade motif are indicated in italic.

Figure 11A:
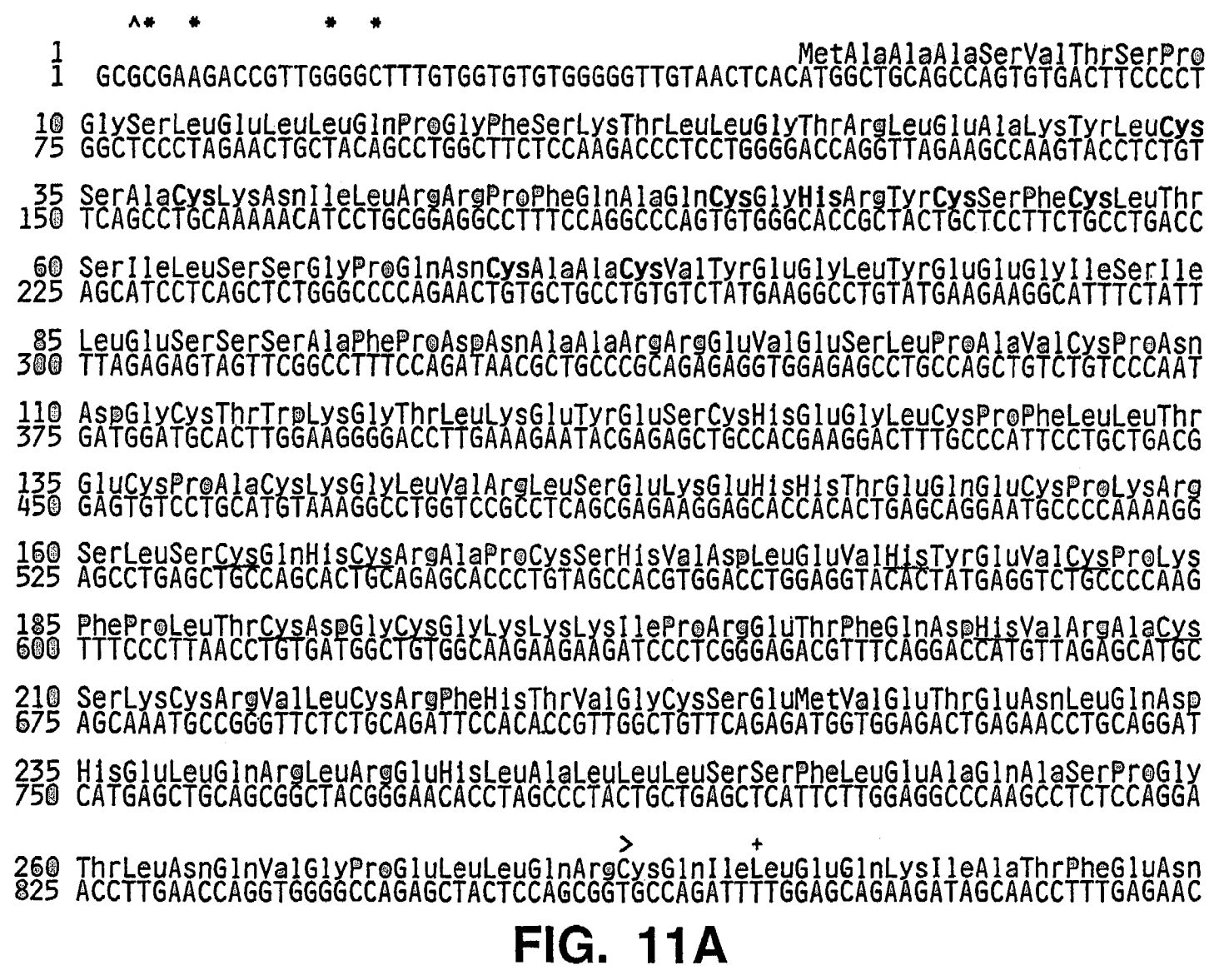
Figure 11B:
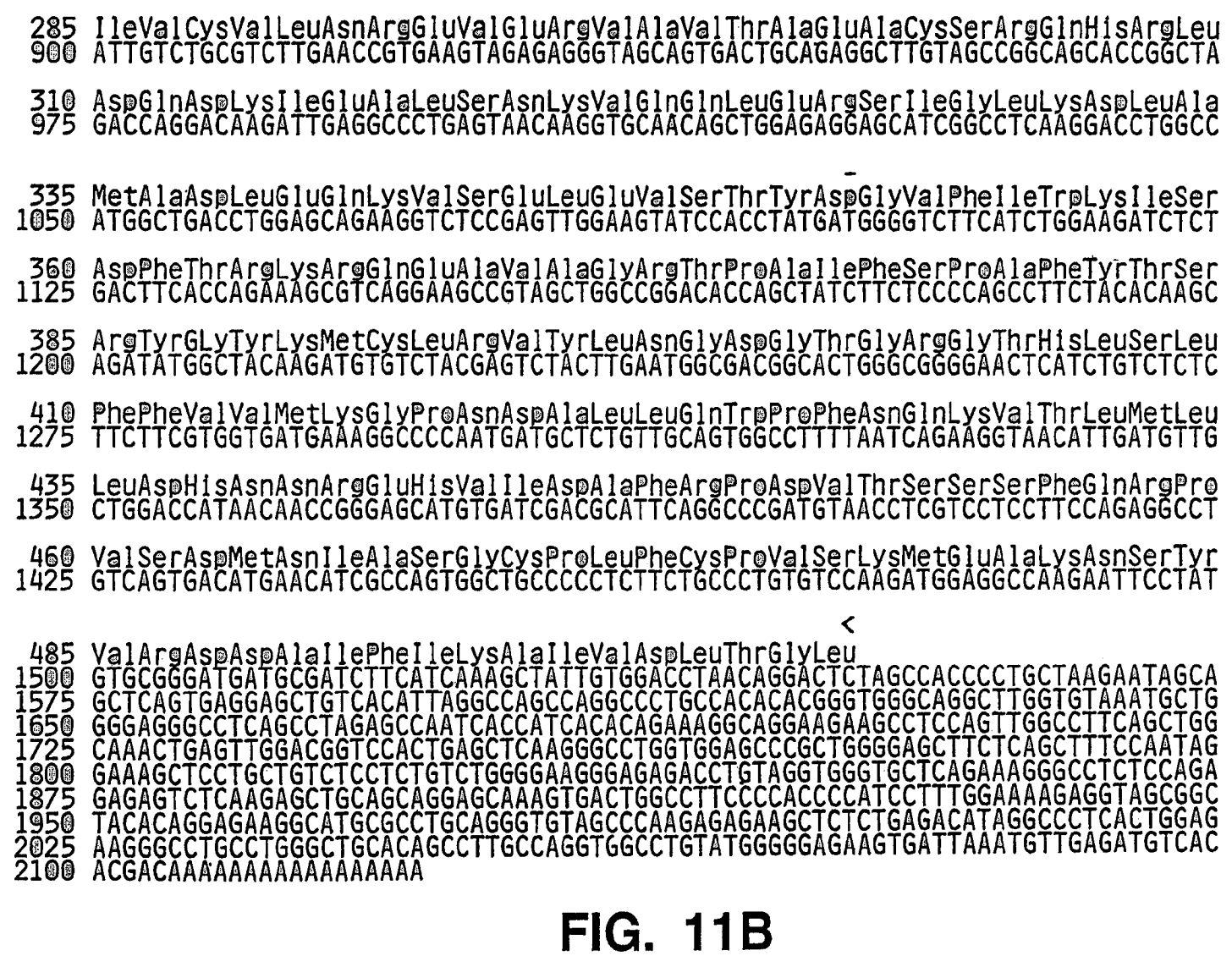

FIG. 11A-11B. Nucleotide and predicted amino acid sequence of the TRAF2 cDNA (SEQ. ID. NOS: 3 and 4).

The nucleic acid sequence of the longest TRAF2 cDNA is shown with numbering starting from the first base after the SalI cloning linker. In addition, the first nucleotide of four independently isolated pPC86 cDNA inserts (*) and the longest λ phage cDNA insert (^) is indicated. The deduced protein sequence is displayed above with numbering from the putative initiation methionine, which is in-frame with the GAL4 activation domain coding region in all isolated pPC86TRAF2 cDNA clones (see text). Cysteine and histidine residues defining the RING finger motif and the two TFIIIA-like zinc finger motifs (see text) are indicated in bold or underlined, respectively. The TRAF domain (see text) comprises amino acids 272 (>)-501 (<). The potential leucine zipper region (see text) extends between amino acids 275 (+)-351 (−). Amino acids within this region defining the heptade motif are indicated in italic.

FIG. 12A-12B. Sequence similarity of regions in TRAF2 to zinc-binding motifs.

(A) Comparison of amino acid sequences containing RING finger motifs. The TRAF2 RING finger motif is aligned with the respective zinc-binding motifs of the regulatory protein COP1 from *A. thaliana* (Deng et al., *Cell* 71, 791-801 [1992]; SEQ. ID. NO: 5), the human estrogen-responsive finger protein EFP (Inoue et al., *Proc. Natl. Acad. Sci. USA* 90, 11117-11121 [1993]; SEQ. ID. NO: 6), the RAD18 and UVS-2 gene products required for DNA repair in *S. cerevisiae* and *N. crassa*, respectively (Jones et al., *Nucl. Acids Res.* 16, 7119-7131 [1988]; SEQ. ID. NO: 7; Tomita et al., *Mol. Gen. Genet.* 238, 225-233 [1993]; SEQ. ID. NO: 8), the human V(D)J recombination activating gene product RAG-1 (Schatz et al., *Cell* 59, 1035-1048 [1989]; SEQ. ID. NO: 9), the human 52 kd riboculeoprotein SS-A/Ro (Chan et al., *J. Clin. Invest.* 87, 68-76 [1987]; Itoh et al., *J. Clin. Invest.* 87, 177-186 [1987]; $A^{52}$ in ref. 1 is $P^{52}$ in ref 2; SEQ. ID. NO: 10); human RING1 (Lovering, GBTRANS accession number Z14000 [1992]; SEQ. ID. NO: 11), mouse T lymphocyte regulatory protein RPT-1 (Patarca et al., *Proc. Natl. Acad. Sci. USA* 85, 2733-2737 [1988]; SEQ. ID. NO: 12), human regulatory protein RFP (Takahashi et al., *Mol. Cell. Biol.* 8, 1853-1856 [1988]; SEQ. ID. NO: 13), and the product of the human proto-oncogen c-cbl (Blake et al., *Oncogene* 6, 653-657 [1991]; SEQ. ID. NO: 14).

(B) Comparison of amino acid sequences containing TFIIIA-type zinc finger motifs. A region in TRAF2 comprising two contiguous repeats of the consensus sequence $^C/_H$-$X_{2-4}$-$^C/_H$-$X_{2-15}$-$^C/_H$-$X_{2-4}$-$^C/_H$ (Berg, *J. Biol. Chem.* 265, 6513-6516 [1990]) is aligned with similar zinc-binding motifs of the developmentally regulated DG17 gene product from *D. discoideum* (Driscoll & Williams, *Mol. Cell. Biol.* 7, 4482-4489 [1987]; SEQ. ID. NO: 15), the transcription factor IIIA form *X. laevis* (Miller et al., *EMBO J.* 4, 1609-1614 [1985]; SEQ. ID. NO: 16), the *Xenopus* zinc finger proteins XLCOF14 and XFIN (Nietfeld et al., *J. Mol. Biol.* 208, 639-659 [1989]; SEQ. ID. NO: 17; Ruiz i Altaba et al., *EMBO J.* 6, 3065-3070 [1987]; SEQ. ID. NO: 18), the mouse ZFY1/2 and MFG2 gene products (Mardon & Page, *Cell* 56, 765-770 [1989]; SEQ. ID. NO: 19; Passananti et al., *Proc. Natl. Acad. Sci. USA* 86, 9421-9471 [1989]; SEQ. ID. NO: 20), and the RAD18 and UVS-2 proteins (see above; SEQ. ID. NOS: 21 and 22).

FIG. 13. Homology between TRAF1 and TRAF2.

An optimized alignment of the protein sequences of TRAF1 and TRAF2 is shown. Identical amino acids are boxed. The C-terminal TRAF domain (see text) comprises amino acids 180-409 of TRAF1 and 272-501 of TRAF2.

Figure 14A:
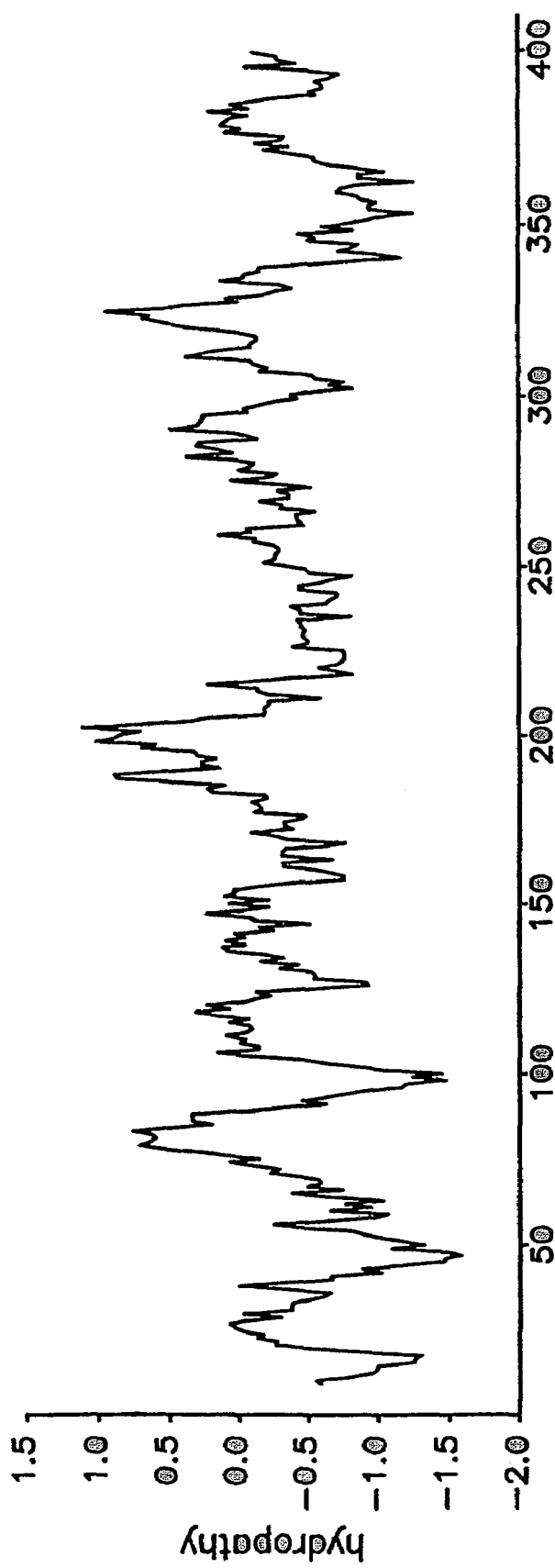
Figure 14B:
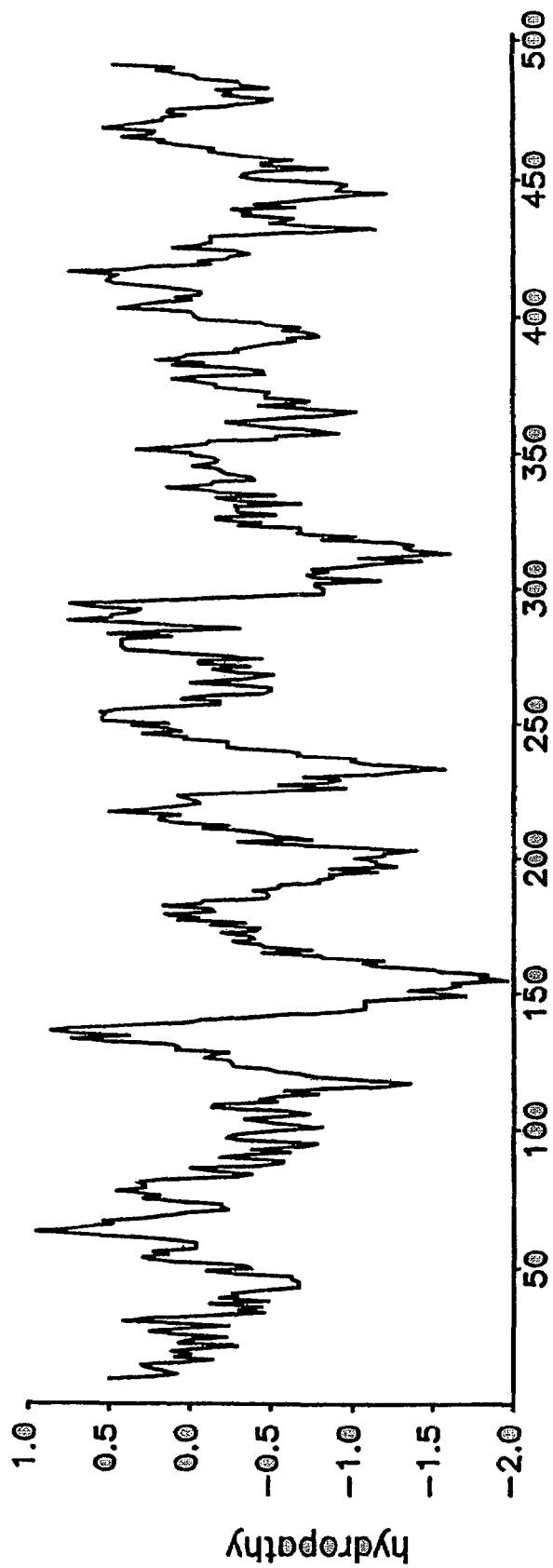

FIG. 14A-14B. Hydropathy analysis of TRAF1 and TRAF2.

Hydropathy profiles of the amino acid sequences of TRAF1 (A) and TRAF2 (B) were obtained by the method of Kyte and Doolittle, *J. Mol. Biol.* 157, 105-132 (1982) using a window of twenty amino acids. The numbers under each plot indicate positions of the amino acids of the respective protein.

Figure 15A:
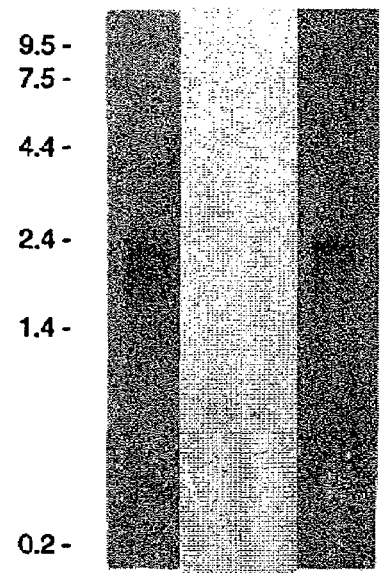
Figure 15B:
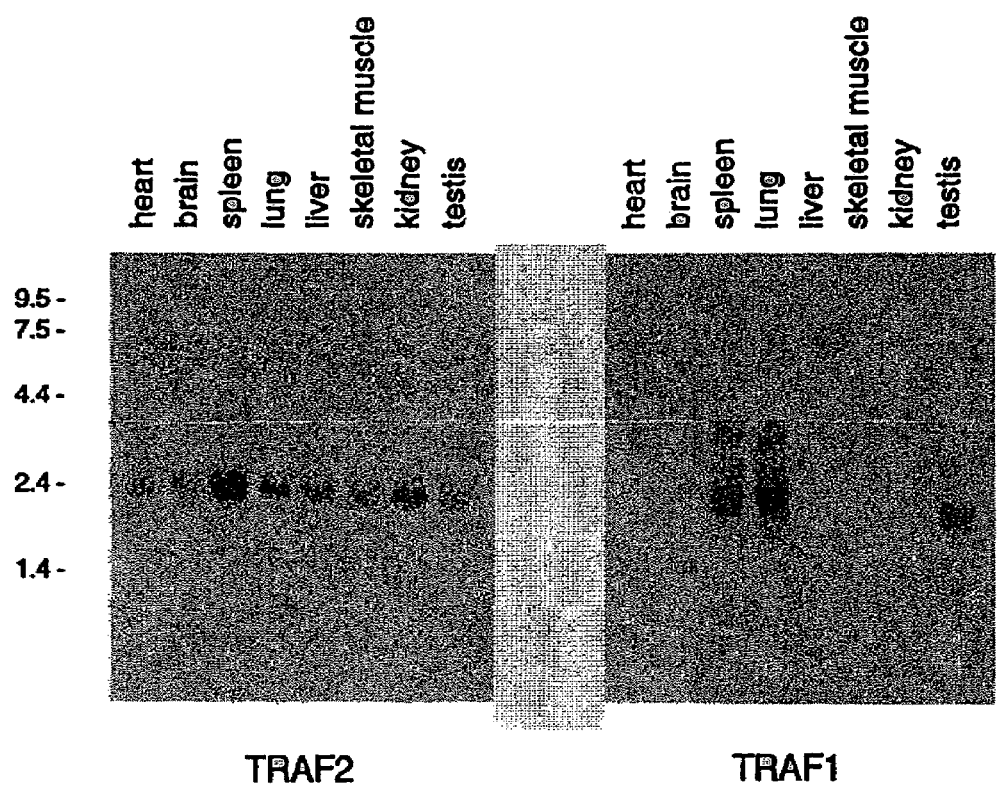

FIG. 15A-15B. Northern blot analysis of TRAF1 and TRAF2 mRNA.

(A) Northern blot analysis of TRAF1 and TRAF2 mRNA in CT6 cells. There is 3 μg of poly(A)$^+$ RNA from CT6 cells per lane.

(B) Northern blot analysis of TRAF1 and TRAF2 mRNA in mouse tissues. Mouse multiple tissue northern blots (Clontech) were hybridized with radiolabeled TRAF1 and TRAF2 probes as described in the text.

Figure 16:
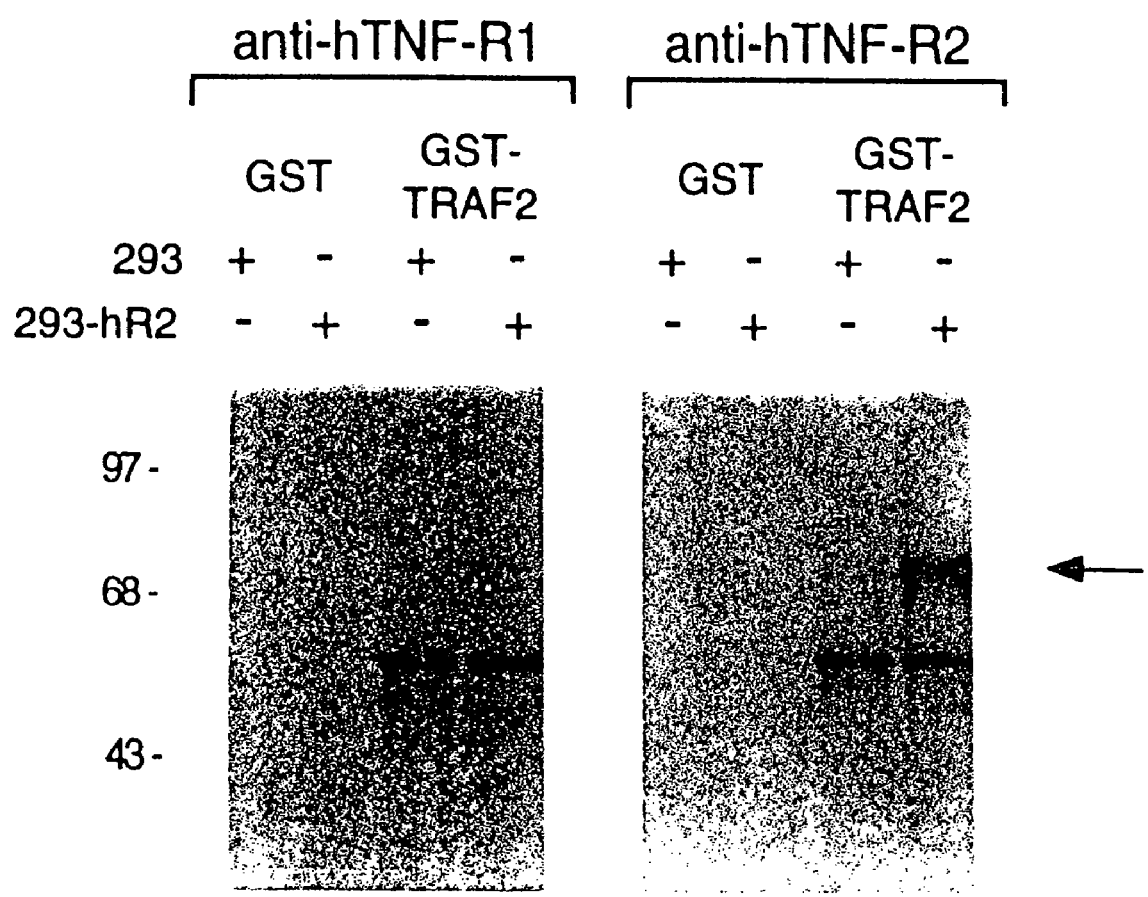

FIG. 16. Coprecipitation of GST-TRAF2 fusion protein in 293 cell extracts.

GST and GST-TRAF2 fusion protein beads were incubated with lysates from 293 and 293/TNF-R2 cells as described in the text. Reactions were analyzed by SDS-PAGE and Western blot analysis using anti-human TNF-R1 monoclonal antibody 986 (0.5 μg/ml) and anti-human TNF-R2 monoclonal antibody 1036 (0.5 μg/ml). An arrow indicates the 75-80 kd hTNF-R2 band that is coprecipitated specifically with the GST-TRAF2 fusion protein. Molecular weight markers are indicated on the right in kd.

DETAILED DESCRIPTION OF THE INVENTION

A. Definitions

The phrases "factor," "tumor necrosis factor receptor associated factor", "TNF-R2 associated factor" and "TRAF" are used interchangeably and refer to a native factor capable of specific association with the intracellular domain of a native TNF-R2, and functional derivatives of such native factor. In the context of this definition the phrase "specific association" is used in the broadest sense, and includes direct binding to a site or region within the intracellular domain of a native TNF-R2 of the human or of any animal species, and indirect association with a native TNF-R2 intracellular domain, mediated by a further molecule, such as another TRAF. The phrase "native TRAF" designates a TRAF polypeptide as occurring in nature in any cell type of any human or non-human animal species, with or without the initiating methionine, whether purified from native source, synthesized, produced by recombinant DNA technology or by any combination of these and/or other methods. Native TRAFs specifically include monomeric, homo- and heterodimeric and homo- and heterooligomeric forms of such naturally occurring polypeptides. The native TRAF polypeptides preferably share a novel sequence motif in the C-terminal portion of their amino acid sequences, and preferably are at least about 40%, more preferably at least about 50%, most preferably at least about 55% homologous within this C-terminal "TRAF domain". The "TRAF domain" encompasses about amino acids 272 to 501 of the native mouse TRAF2 amino acid sequence, about amino acids 180 to 409 of the native mouse TRAF1 amino acid sequence, and homologous domains of other native TRAFs and their functional derivatives.

The terms "native type 2 TNF receptor" and "native TNF-R2" are used interchangeably, and refer to any naturally occurring (native) type 2 TNF receptor from any (human and non-human) animal species, with or without the initiating methionine and with or without a signal sequence attached to the N-terminus, whether purified from native source, synthesized, produced by recombinant DNA technology or by any combination of these and/or other methods.

The terms "native human type 2 TNF receptor" and "native human TNF-R2", which are used interchangeably, refer to a human TNF-R2 having the amino acid sequence disclosed in EP 418,014 (published 20 Mar. 1991), with or without the initiating methionine and with or without a signal sequence attached to the N-terminus, whether purified from native source, synthesized, produced by recombinant DNA technology or by any combination of these and/or other methods, and other naturally occurring human TNF-R2 variants, including soluble and variously glycosylated forms of native full-length human TNF-R2, whether purified from natural sources, synthetically produced in vitro or obtained by genetic manipulation including methods of recombinant DNA technology.

A "functional derivative" of a native polypeptide is a compound having a qualitative biological activity in common with the native polypeptide. Thus, a functional derivative of a native TRAF polypeptide is a compound that has a qualitative biological activity in common with a native TRAF. "Functional derivatives" include, but are not limited to, fragments of native polypeptides from any animal species (including humans), and derivatives of native (human and non-human) polypeptides and their fragments, provided that they have a biological activity in common with a respective native polypeptide. "Fragments" comprise regions within the sequence of a mature native polypeptide. The term "derivative" is used to define amino acid sequence and glycosylation variants, and covalent modifications of a native polypeptide, whereas the term "variant" refers to amino acid sequence and glycosylation variants within this definition. Preferably, the functional derivatives are polypeptides which have at least about 65% amino acid sequence identity, more preferably about 75% amino acid sequence identity, even more preferably at least about 85% amino acid sequence identity, most preferably at least about 95% amino acid sequence identity with the sequence of a corresponding native polypeptide. Most preferably, the functional derivatives of a native TRAF polypeptide retain or mimic the region or regions within the native polypeptide sequence that directly participate in the association with the TNF-R2 intracellular domain and/or in homo- or heterodimerization. The phrase "functional derivative" specifically includes peptides and small organic molecules having a qualitative biological activity in common with a native TRAF.

The term "biological activity" in the context of the definition of functional derivatives is defined as the possession of at least one adhesive, regulatory or effector function qualitatively in common with a native polypeptide (e.g. TRAF). A preferred biological property of the functional derivatives of the native TRAF polypeptides herein is their ability to associate with the intracellular domain of a native TNF-R2 (either by direct binding or via interaction with another TRAF), and thereby mediate or block a biological response signaled (exclusively or partially) by the TNF-R2 with which they are associated.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

The TRAF polypeptides of the present invention specifically include native murine TRAF-1 (SEQ. ID. NO: 2) and native murine TRAF-2 (SEQ. ID. NO: 4) their homo- and heterodimeric and homo- and heterooligomeric forms, and their analogs in other mammalian species, such as rat, porcine, equine, cow, higher primates, and humans, and the functional derivatives of such native polypeptides. The functional derivatives of a native TRAF-1 or native TRAF-2 receptor are preferably encoded by DNAs capable, under stringent conditions, of hybridizing to the complement of a DNA encoding a native TRAF polypeptide. More preferably, the functional derivatives share at least about 40% sequence homology, more preferably at least about 50% sequence homology, even more preferably at least about 55% sequence homology, most preferably at least about 60% sequence homology with any domain, and preferably with the TNF-R2 binding domain(s) and/or the dimerization domain(s), of a native TRAF polypeptide. In a most preferred embodiment, a functional derivative will share at least about 50% sequence homology with the C-terminal TRAF region of murine TRAF2, or are encoded by DNA capable of hybridizing, under stringent conditions, with the complement of DNA encoding the TRAF region of murine TRAF2.

The "stringent conditions" are overnight incubation at 42° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA.

The terms "amino acid" and "amino acids" refer to all naturally occurring L-α-amino acids. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids
  Acidic Residues: aspartic acid, glutamic acid
  Basic Residues: lysine, arginine, histidine II. Uncharged Amino Acids
  Hydrophilic Residues: serine, threonine, asparagine, glutamine
  Aliphatic Residues: glycine, alanine, valine, leucine, isoleucine
  Non-polar Residues: cysteine, methionine, proline
  Aromatic Residues: phenylalanine, tyrosine, tryptophan The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

The term "glycosylation variant" is used to refer to a glycoprotein having a glycosylation profile different from that of a native counterpart or to glycosylated variants of a polypeptide unglycosylated in its native form(s). Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation.

Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651-663 [1985]; Novotny and Haber, *Proc. Natl. Acad. Sci. USA* 82, 4592-4596 [1985]).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al., *Sequences of Proteins of Immunological Interest*, National Institute of Health, Bethesda, Md. [1991]). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Natl. Acad. Sci. USA* 81, 6851-6855 [1984]).

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522-525 [1986]; Reichmann et al., *Nature* 332, 323-329 [1988]; and Presta, *Curr. Op. Struct. Biol.* 2593-596 [1992]).

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

"Transformation" means introducing DNA into an organism so that the DNA is replicable, either as an extrachromosomal element or by chromosomal integration.

"Transfection" refers to the taking up of an expression vector by a host cell whether or not any coding sequences are in fact expressed.

The terms "transformed host cell" and "transformed" refer to the introduction of DNA into a cell. The cell is termed a "host cell", and it may be a prokaryotic or a eukaryotic cell. Typical prokaryotic host cells include various strains of *E. coli*. Typical eukaryotic host cells are mammalian, such as Chinese hamster ovary cells or human embryonic kidney 293 cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published 4 May 1988, or via deoxynucleoside H-phosphanate intermediates as described by Froehler et al., *Nucl. Acids Res.* 14, 5399 (1986)]. They are then purified on polyacrylamide gels.

B. Identification and Purification of TRAFs

The native TRAF polypeptides can be identified in and purified from certain tissues known to possess a type 2 TNF receptor (TNF-R2) mRNA and to express it at a detectable level. Thus, murine TRAF can, for example, be obtained from the murine interleukin 2 (IL-2)-dependent cytotoxic T cell line CT6 (Ranges et al. *J. Immunol.* 142, 1203-1208 (1989)). Murine TRAF1 can also be purified from spleen, lung and testis; whereas murine TRAF2 can be isolated and purified from an even larger variety of tissues, including heart, brain, spleen, lung, liver, skeletal muscle, kidney and testis (see FIG. 15B). In general, TRAF proteins are expected to be expressed in human tissues that are known to express TNF-R2, although not all of such tissues will express all TRAFs. Alternatively, TRAF polypeptides can be isolated from cell lines transfected with DNA encoding a native TNF-R2 or a TNF-R2 derivative comprising intracellular domain sequences participating in the interaction with TRAFs. Factors that are associated with the intracellular domain of a native TNF-R2 can be identified by immunoprecipitation of the receptor or receptor derivative from cells expressing it. Immunoprecipitation in general consists of multiple ordered steps, including lysing the cell with detergent if the TNF-R2 is membrane-bound, binding of TNF-R2 to an anti-TNF-R2 antibody, precipitating the antibody complex, washing the precipitate, and dissociating TNF-R2 and any associated factor from the immune complex. The dissociated factor(s) can then be analyzed by electrophoretic methods. In a preferred embodiment, radiolabeled TNF-R2 (or a derivative) is immunoprecipitated with protein A-agarose (Oncogene Science) or with protein A-Sepharose (Pharmacia). In this case, the TNF-R2/anti-TNF-R2 antibody immune complexes are precipitated by *Staphylococcus aureus* protein A bound to the agarose or Sepharose. The immunoprecipitate is then analyzed by autoradiography or by fluorography, depending on the actual radiolabel used. The TRAF proteins (which are characterized by their ability to associate with the intracellular domain of TNF-R2) will coprecipitate with the receptor or receptor derivative, and can be further purified by methods known in the art, such as purification on an affinity column.

A large-scale purification scheme for purifying factors that associate with the intracellular domain of TNF-R2 takes advantage of plasmid expression vectors that direct the synthesis of foreign polypeptides in *E. coli* as fusions with the C terminus of glutathione S-transferase (GST), as described by Smith, D. B. and Johnson, K. S., *Gene* 67 31-40 (1988). The intracellular domain of TNF-R2 is expressed as a fusion protein with GST in *E. coli* recombinant host cells, and can be purified from crude bacterial lysates by absorption on glutathione-agarose beads (Sigma). A cell lysate containing the factor(s) to be purified is then applied to a GST-TNF-R2 fusion protein affinity column. Protein(s) bound to the column is/are eluted, precipitated and isolated by SDS-PAGE under reducing conditions, and visualized by silver staining. GST gene fusion vectors (pGEX vectors) as well as kits for cloning and expression of GST fusion systems are commercially available from Pharmacia (see Pharmacia Catalog, 1994, pages 133; and 142-143).

Purified protein can be either sequenced directly by automated Edman degradation with a model 470A Applied Biosystems gas phase sequencer equipped with a 120A PTH amino acid analyzer or sequenced after digestion with various chemicals or enzymes. PTH amino acids were integrated using a ChromPerfect data system (Justice Innovations, Palo Alto, Calif.). Sequence interpretation can be performed on a VAX 11/785 Digital Equipment Corporation computer as described by Henzel et al., *J. Chromatography* 404, 41 (1987). In some cases, eluates electrophoresed on SDS polyacrylamide gels are electrotransferred to a PVDF membrane (ProBlott, ABI, Foster City, Calif.) and stained with Coomassie Brilliant Blue R250 (Sigma). The specific protein is excised from the blot for N-terminal sequencing. To determine internal protein sequences, purified fractions obtained by reverse phase capillary HPLC are typically dried under vacuum (SpeedVac), resuspended in appropriate buffers, and digested with cyanogen bromide, and/or various proteases, such as trypsin, the lysine-specific enzyme Lys-C (Wako Chemicals, Richmond, Va.) or Asp-N (Boehringer Mannheim, Indianapolis, Ind.). After digestion, the resultant peptides are sequenced as a mixture or are resolved by HPLC.

C. Recombinant Production of TRAF Polypeptides

Preferably, the TRAF polypeptides are prepared by standard recombinant procedures by culturing cells transfected to express TRAF polypeptide nucleic acid (typically by transforming the cells with an expression vector) and recovering the polypeptide from the cells. However, it is envisioned that the TRAF polypeptides may be produced by homologous recombination, or by recombinant production methods utilizing control elements introduced into cells already containing DNA encoding an TRAF polypeptide. For example, a powerful promoter/enhancer element, a suppressor, or an exogenous transcription modulatory element may be inserted in the genome of the intended host cell in proximity and orientation sufficient to influence the transcription of DNA encoding the desired TRAF polypeptide. The control element does not encode the TRAF polypeptide, rather the DNA is indigenous to the host cell genome. One next screens for cells making the polypeptide of this invention, or for increased or decreased levels of expression, as desired.

Thus, the invention contemplates a method for producing a TRAF polypeptide comprising inserting into the genome of a cell containing nucleic acid encoding a TRAF polypeptide a transcription modulatory element in sufficient proximity and orientation to the nucleic acid molecule to influence transcription thereof, with an optional further step of culturing the cell containing the transcription modulatory element and the nucleic acid molecule. The invention also contemplates a host cell containing the indigenous TRAF polypeptide nucleic acid molecule operably linked to exogenous control sequences recognized by the host cell.

1. Isolation of DNA Encoding the TRAF Polypeptides

For the purpose of the present invention, DNA encoding a TRAF polypeptide can be obtained from cDNA libraries prepared from tissue believed to possess a type 2 TNF receptor (TNF-R2) mRNA and to express it at a detectable level. For example, cDNA library can be constructed by obtaining polyadenylated mRNA from a cell line known to express TNF-R2, and using the mRNA as a template to synthesize double stranded cDNA. Human and non-human cell lines suitable for this purpose have been listed hereinabove. It is noted, however, that TNF-R2 is known to be expressed in a large variety of further tissues which can all potentially serve as a source of TRAF cDNA, even though not all members of the TRAF family will be expressed in all TNF-R2 expressing tissues. Alternatively, DNA encoding new TRAF polypeptides can be obtained from cDNA libraries prepared from tissue known to express a previously identified TRAF polypeptide at a detectable level. The TRAF polypeptide genes can also be obtained from a genomic library, such as a human genomic cosmid library.

Libraries, either cDNA or genomic, are screened with probes designed to identify the gene of interest or the protein encoded by it. For cDNA expression libraries, suitable probes include monoclonal and polyclonal antibodies that recognize and specifically bind to a TRAF polypeptide. For cDNA libraries, suitable probes include carefully selected oligonucleotide probes (usually of about 20-80 bases in length) that encode known or suspected portions of a TRAF polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10-12 of Sambrook et al., *Molecular Cloning: A Laboratory Manual*, New York, Cold Spring Harbor Laboratory Press, 1989).

A preferred method of practicing this invention is to use carefully selected oligonucleotide sequences to screen cDNA libraries from various tissues. The oligonucleotide sequences selected as probes should be sufficient in length and sufficiently unambiguous that false positives are minimized. The actual nucleotide sequence(s) is/are usually designed based on regions of a TRAF which have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding TRAFs can also be identified and isolated by other known techniques of recombinant DNA technology, such as by direct expression cloning or by using the polymerase chain reaction (PCR) as described in U.S. Pat. No. 4,683,195, issued 28 Jul. 1987, in section 14 of Sambrook et al., *Molecular Cloning: A Laboratory Manual*, second edition, Cold Spring Harbor Laboratory Press. New York, 1989, or in Chapter 15 *of Current Protocols in Molecular Biology*, Ausubel et al. eds., Greene Publishing Associates and Wiley-Interscience 1991. This method requires the use of oligonucleotide probes that will hybridize to DNA encoding a TRAF.

According to a preferred method for practicing the invention, the coding sequences for TRAF proteins can be identified in a recombinant cDNA library or a genomic DNA library based upon their ability to interact with the intracellular domain of a TNF-R2. For this purpose one can use the yeast genetic system described by Fields and co-workers (Fields and Song, *Nature* (London) 340, 245-246 [1989]; Chien et al., *Proc. Natl. Acad. Sci. USA* 88, 9578-9582 [1991]) as disclosed by Chevray and Nathans (*Proc. Natl. Acad. Sci. USA* 89, 5789-5793 [1991]). Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

To directly isolate genes encoding proteins that associate with the intracellular domain of TNF-R2, DNA encoding a TNF-R2 intracellular domain or a fragment thereof is cloned into a vector containing DNA encoding the DNA-binding domain of GAL4. A plasmid cDNA library is then constructed by cloning double-stranded cDNA encoding a candidate factor in a vector comprising DNA encoding the GAL4 transcriptional activation domain. Thereafter, yeast cells containing reporter genes are cotransformed with the TNF-R2-GAL4 DNA binding domain vector and with library plasmid DNA. Typically, an *S. cerevisiae* cell containing two reporter genes: lacZ(βgal) and H is genes, serves as a host for cotransformation. Yeast transformants are selected by plating on supplemented synthetic dextrose medium lacking tryptophan, leucine and histidine, and protein-protein interactions are monitored by the yeast colony filter β-galactosidase assay, essentially as described by Chevray and Nathans, supra. Only colonies with protein-protein interaction will grow on his⁻ plates, and are then analyzed for β-gal as a further control.

Once cDNA encoding a TRAF from one species has been isolated, cDNAs from other species can also be obtained by cross-species hybridization. According to this approach, human or other mammalian cDNA or genomic libraries are probed by labeled oligonucleotide sequences selected from known TRAF sequences (such as murine TRAF-1 and TRAF-2 as disclosed in the present application) in accord with known criteria, among which is that the sequence should be sufficient in length and sufficiently unambiguous that false positives are minimized. Typically, a $^{32}P$-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid.

Once the sequence is known, the gene encoding a particular TRAF polypeptide can also be obtained by chemical synthesis, following one of the methods described in Engels and Uhlmann, *Agnew. Chem. Int. Ed. Engl.* 28, 716 (1989). These methods include triester, phosphite, phosphoramidite and H-phosphonate methods, PCR and other autoprimer methods, and oligonucleotide syntheses on solid supports.

2. Amino Acid Sequence Variants of a Native TRAF Proteins or Fragments

Amino acid sequence variants of native TRAFs and TRAF fragments are prepared by methods known in the art by introducing appropriate nucleotide changes into a native or variant TRAF DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the TRAF, the amino acid sequence variants of TRAF are preferably constructed by mutating the DNA, either to arrive at an allele or an amino acid sequence variant that does not occur in nature.

One group of the mutations will be created within the domain or domains identified as being involved in the interaction with the intracellular domain of TNF-R2. TRAF variants mutated to enhance their association (binding or indirect association) with TNF-R2 will be useful as inhibitors of native TNF-R2/native TNF interaction. In addition, such variants will be useful in the diagnosis of pathological conditions association with the overexpression of TNF-R2, and in the purification of TNF-R2. A target for such mutations is the N-terminal RING finger domain of TRAF2 and related factors, as this domain is believed to be involved in the interaction with the intracellular domain of TNF-R2.

Another group of mutations will be performed within region(s) involved in interactions with other TNF-R2 associated factors. Thus, amino acid alterations within the homologous C-terminal domains (protein dimerization motif) of TRAF 1, TRAF2 and other factors of the TRAF family can enhance the ability of such factors to form stable dimers which are required for signaling through the TNF-R2 receptor.

Alternatively or in addition, amino acid alterations can be made at sites that differ in TRAF proteins from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1-3.

One helpful technique is called "alanine scanning" (Cunningham and Wells, *Science* 244, 1081-1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding a TRAF variant can, for example, be obtained by chemical synthesis as hereinabove described.

More preferably, DNA encoding a TRAF amino acid sequence variant is prepared by site-directed mutagenesis of DNA that encodes an earlier prepared variant or a nonvariant version of the TRAF. Site-directed (site-specific) mutagenesis allows the production of TRAF variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487-6500 [1982]). Also, plasmid vectors that contain a single-stranded phage origin of replication (Veira et al., *Meth. Enzymol.* 153, 3 [1987]) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of a TRAF. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 μl. The reaction mixture is overlayered with 35 µl mineral oil. The reaction is denatured for 5 minutes at 100° C., placed briefly on ice, and then 1 µl *Thermus aquaticus* (Taq) DNA polymerase (5 units/1), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C.,
30 sec. 72° C., then 19 cycles of the following:
30 sec. 94° C.,
30 sec. 55° C., and
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)]. The starting material is the plasmid (or vector) comprising the TRAF DNA to be mutated. The codon(s) within the TRAF to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the TRAF DNA. After the restriction sites have been introduced into the plasmid, the plasmid is cut at these sites to linearize it. A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated TRAF DNA sequence.

Additionally, the so-called phagemid display method may be useful in making amino acid sequence variants of native or variant TRAFs or their fragments. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Further details of the foregoing and similar mutagenesis techniques are found in general textbooks, such as, for example, Sambrook et al., supra, and *Current Protocols in Molecular Biology*, Ausubel et al. eds., supra.

Naturally-occurring amino acids are divided into groups based on common side chain properties:

(1) hydrophobic: norleucine, met, ala, val, leu, ile;
(2) neutral hydrophobic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant, and may result in TRAF variants which block TNF biological activities, especially if they are exclusively or primarily mediated by TNF-R2. Amino acid positions that are conserved among various species and/or various receptors of the TRAF family are generally substituted in a relatively conservative manner if the goal is to retain biological function.

Amino acid sequence deletions generally range from about 1 to 30 residues, more preferably about 1 to 10 residues, and typically are contiguous. Deletions may be introduced into regions not directly involved in the interaction with the TNF-R2 intracellular domain.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the TRAF protein amino acid sequence) may range generally from about 1 to 10 residues, more preferably 1 to 5 residues, more preferably 1 to 3 residues. Examples of terminal insertions include the TRAF polypeptides with an N-terminal methionyl residue, an artifact of its direct expression in bacterial recombinant cell culture, and fusion of a heterologous N-terminal signal sequence to the N-terminus of the TRAF molecule to facilitate the secretion of the mature TRAF from recombinant host cells. Such signal sequences will generally be obtained from, and thus homologous to, the intended host cell species. Suitable sequences include STII or Ipp for *E. coli*, alpha factor for yeast, and viral signals such as herpes gD for mammalian cells.

Other insertional variants of the native TRAF molecules include the fusion of the N- or C-terminus of the TRAF molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on 6 Apr. 1989.

Since it is often difficult to predict in advance the characteristics of a variant TRAF, it will be appreciated that some screening will be needed to select the optimum variant.

3. Insertion of DNA into a Cloning Vehicle

Once the nucleic acid encoding a native or variant TRAF is available, it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the TRAF molecule that is inserted into the vector. If the signal sequence is heterologous, it should be selected such that it is recognized and processed (i.e. cleaved by a signal peptidase) by the host cell.

As the TRAF molecules are intracellular proteins, they are unlikely to have a native signal sequence. Heterologous signal sequences suitable for prokaryotic host cells are prokaryotic signal sequences, such as the alkaline phosphatase, penicillinase, lpp, or heat-stable enterotoxin II leaders. For yeast secretion the yeast invertase, alpha factor, or acid phosphatase leaders may be used. In mammalian cell expression mammalian signal sequences are suitable.

(ii) Origin of Replication Component

Both expression and cloning vectors contain a nucleic acid sequence that enabled the vector to replicate in one or more selected host cells. Generally, in cloning vectors this sequence is one that enables the vector to replicate independently of the host chromosomes, and includes origins of replication or autonomously replicating sequences. Such sequence are well known for a variety of bacteria, yeast and viruses. The origin of replication from the well-known plasmid pBR322 is suitable for most gram negative bacteria, the 2µ plasmid origin for yeast and various viral origins (SV40, polyoma, adenovirus, VSV or BPV) are useful for cloning vectors in mammalian cells. Origins of replication are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA is also cloned by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of the DNA encoding the desired heterologous polypeptide. However, the recovery of genomic DNA is more complex than that of an exogenously replicated vector because restriction enzyme digestion is required to excise the encoded polypeptide molecule.

(iii) Selection Gene Component

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin [Southern et al., *J. Molec. Appl. Genet.* 1, 327 (1982)], mycophenolic acid [Mulligan et al., *Science* 209, 1422 (1980)], or hygromycin [Sudgen et al., *Mol. Cel. Biol.* 5, 410-413 (1985)]. The three examples given above employ bacterial genes under eukaryotic control to convey resistance to the appropriate drug G418 or neomycin (geneticin), xgpt (mycophenolic acid), or hygromycin, respectively.

Other examples of suitable selectable markers for mammalian cells are dihydrofolate reductase (DHFR) or thymidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Nat'l. Acad. Sci. USA* 77, 4216 (1980). A particularly useful DHFR is a mutant DHFR that is highly resistant to MTX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp1 gene present in the yeast plasmid YRp7 (Stinchcomb et al., 1979, *Nature* 282:39; Kingsman et al., 1979, *Gene* 7:141; or Tschemper et al., 1980, *Gene* 10: 157). The trp1 gene provides a selection marker for a mutant strain of yeast lacking the ability to grow in tryptophan, for example, ATCC No. 44076 or PEP4-1 (Jones, 1977, *Genetics* 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(iv) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for a TRAF polypeptide is not usable. However, heterologous promoters generally will result in greater transcription and higher yields of expressed TRAFs as compared to the native TRAF promoters.

Promoters suitable for use with prokaryotic hosts include the β-lactamase and lactose promoter systems (Chang et al., *Nature* 275:615 (1978); and Goeddel et al., *Nature* 281:544 (1979)), alkaline phosphatase, a tryptophan (trp) promoter system (Goeddel, *Nucleic Acids Res.* 8:4057 (1980) and EPO Appln. Publ. No. 36,776) and hybrid promoters such as the tac promoter (H. de Boer et al., *Proc. Nat'l. Acad. Sci. USA* 80:21-25 (1983)). However, other known bacterial promoters are suitable. Their nucleotide sequences have been published, thereby enabling a skilled worker operably to ligate them to DNA encoding TRAF (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding a TRAF.

Suitable promoting sequences for use with yeast hosts include the promoters for 3-phosphoglycerate kinase (Hitzeman et al. *J. Biol. Chem.* 255:2073 (1980)) or other glycolytic enzymes (Hess et al., *J. Adv. Enzyme Reg.* 7:149 (1978); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

TRAF transcription from vectors in mammalian host cells may be controlled by promoters obtained from the genomes of viruses such as polyoma virus, fowlpox virus (UK 2,211, 504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the TRAF sequence, provided such promoters are compatible with the host cell systems.

The early and late promoters of the SV40 virus are conveniently obtained as an SV40 restriction fragment which also contains the SV40 viral origin of replication [Fiers et al., *Nature* 273:113 (1978), Mulligan and Berg, *Science* 209, 1422-1427 (1980); Pavlakis et al., *Proc. Natl. Acad. Sci. USA* 78, 7398-7402 (1981)]. The immediate early promoter of the human cytomegalovirus is conveniently obtained as a HindIII L restriction fragment [Greenaway et al., *Gene* 18, 355-360 (1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., *Nature* 295, 503-508 (1982) on expressing cDNA encoding human immune interferon in monkey cells; Reyes et al., *Nature* 297, 598-601 (1982) on expressing human β-interferon cDNA in mouse cells under the control of a thymidine kinase promoter from herpes simplex virus; Canaani and Berg, *Proc. Natl. Acad. Sci. USA* 79, 5166-5170 (1982) on expression of the human interferon β1 gene in cultured mouse and rabbit cells; and Gorman et al., *Proc. Natl. Acad. Sci., USA* 79, 6777-6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

(v) Enhancer Element Component

Transcription of a DNA encoding the TRAFs of the present invention by higher eukaryotes is often increased by inserting an enhancer sequence into the vector. Enhancers are cisacting elements of DNA, usually about from 10 to 300 bp, that act on a promoter to increase its transcription. Enhancers are relatively orientation and position independent having been found 5' [Laimins et al., *Proc. Natl. Acad. Sci. USA* 78, 993 (1981)] and 3' [Lasky et al., *Mol. Cel. Biol.* 3, 1108 (1983)] to the transcription unit, within an intron [Banerji et al., *Cell* 33, 729 (1983)] as well as within the coding sequence itself [Osborne et al., *Mol. Cel. Biol.* 4, 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297, 17-18 (1982) on enhancing elements for activation of eukaryotic promoters. The enhancer may be spliced into the vector at a position 5' or 3' to the TRAF DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the TRAF. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9, 309 (1981) or by the method of Maxam et al., *Methods in Enzymology* 65, 499 (1980).

Particularly useful in the practice of this invention are expression vectors that provide for the transient expression in mammalian cells of DNA encoding a TRAF. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a TRAF.

Other methods, vectors, and host cells suitable for adaptation to the synthesis of the TRAF polypeptides in recombinant vertebrate cell culture are described in Getting et al., *Nature* 293, 620-625 (1981); Mantel et al., *Nature* 281, 40-46 (1979); Levinson et al.; EP 117,060 and EP 1 17,058. A particularly useful plasmid for mammalian cell culture expression of the TRAF polypeptides is pRK5 (EP 307,247).

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequences by the methods of Messing et al., *Nuclei Acids Res.* 9, 309 (1981) or by the method of Maxam et al., *Methods in Enzymology* 65, 499 (1980).

(viii) Transient Expression Vectors

Particularly useful in the practice of this invention are expression vectors that provide for the transient expression in mammalian cells of DNA encoding a TRAF polypeptide. In general, transient expression involves the use of an expression vector that is able to replicate efficiently in a host cell, such that the host cell accumulates many copies of the expression vector and, in turn, synthesizes high level of a desired polypeptide encoded by the expression vector. Sambrook et al., supra, pp. 16.17-16.22. Transient expression systems, comprising a suitable expression vector and a host cell, allow for the convenient positive screening of such polypeptides for desired biological or physiological properties. Thus transient expression systems are particularly useful in the invention for purposes of identifying analogs and variants of native TRAF polypeptides with TRAF biological activity.

(ix) Suitable Exemplary Vertebrate Cell Vectors

Other methods, vectors, and host cells suitable for adaptation to the synthesis of a TRAF polypeptide (including functional derivatives of native proteins) in recombinant vertebrate cell culture are described in Gething et al., *Nature* 293, 620-625 (1981); Mantei et al., *Nature* 281, 40-46 (1979); Levinson et al., EP 117,060; and EP 117,058. A particularly useful plasmid for mammalian cell culture expression of a TRAF polypeptide is pRK5 (EP 307,247) or pSV16B (PCT Publication No. WO 91/08291).

D. Selection and Transformation of Host Cells

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B. *E. coli* X1776 (ATCC 31,537), *E. coli* W3110 (ATCC 27,325), *Pseudomonas* species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromvces lactis* [Louvencourt et al., *J. Bacteriol.* 737 (1983)]; *yarrowia* (EP 402,226); *Pichia pastoris* (EP 183, 070), *Trichoderma reesia* (EP 244,234), *Neurospora crassa* [Case et al., *Proc. Natl. Acad. Sci. USA* 76, 5259-5263 (1979)]; and *Aspergillus* hosts such as *A. nidulans* [Ballance et al., *Biochem. Biophys. Res. Commun.* 112, 284-289 (1983); Tilburn et al., *Gene* 26, 205-221 (1983); Yelton et al., *Proc. Natl. Acad. Sci. USA* 81, 1470-1474 (1984)] and *A. niger* [Kelly and Hynes, *EMBO J.* 4, 475-479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g. Luckow et al., *Bio/Technology* 6, 47-55 (1988); Miller et al., in *Genetic Engineering*, Setlow, J. K. et al., eds., Vol. 8 (Plenum Publishing, 1986), pp. 277-279; and Maeda et al., *Nature* 315, 592-594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the TRAF DNA. During incubation of the plant cell culture with *A. tumefaciens*, the DNA encoding a TRAF is transferred to the plant cell host such that it is transfected, and will, under appropriate conditions, express the TRAF DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, Biol. Reprod. 23, 243-251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TR1 cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly preferred host cells for the purpose of the present invention are vertebrate cells producing the TRAF polypeptides.

Host cells are transfected and preferably transformed with the above-described expression or cloning vectors and cultured in conventional nutrient media modified as is appropriate for inducing promoters or selecting transformants containing amplified genes.

E. Culturing the Host Cells

Prokaryotes cells used to produced the TRAF polypeptides of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat. Nos. 4,767,704; 4,657,866; 4,927,762; or 4,560,655; WO 90/03430; WO 87/00195 or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the TRAF polypeptides of this invention may be produced by homologous recombination, or with recombinant production methods utilizing control elements introduced into cells already containing DNA encoding the particular TRAF.

F. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA* 77, 5201-5205 (1980)], dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734-738 (1980).

Antibodies useful for immunohistochemical staining and/or assay of sample fluids may be either monoclonal or polyclonal, and may be prepared in any animal. Conveniently, the antibodies may be prepared against a native TRAF polypeptide, or against a synthetic peptide based on the DNA sequence provided herein as described further hereinbelow.

G. Purification of the TRAF Polypeptides

The TRAF polypeptide is typically recovered from host cell lysates.

When the TRAF polypeptide is expressed in a recombinant cell other than one of human origin, the TRAF is completely free of proteins or polypeptides of human origin. However, it is necessary to purify the TRAF protein from recombinant cell proteins or polypeptides to obtain preparations that are substantially homogenous as to the TRAF. As a first step, the culture medium or lysate is centrifuged to remove particulate cell debris. The membrane and soluble protein fractions are then separated. The TRAF protein may then be purified from the soluble protein fraction. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG. Specific purification procedures have been described hereinabove.

TRAF functional derivatives in which residues have been deleted, inserted and/or substituted are recovered in the same fashion as the native receptor chains, taking into account of any substantial changes in properties occasioned by the alteration. For example, fusion of the TRAF protein with another protein or polypeptide, e.g. a bacterial or viral antigen, facilitates purification; an immunoaffinity column containing antibody to the antigen can be used to absorb the fusion. Immunoaffinity columns such as a rabbit polyclonal anti-TRAF column can be employed to absorb TRAF variant by binding to at least one remaining immune epitope. A protease inhibitor, such as phenyl methyl sulfonyl fluoride (PMSF) also may be useful to inhibit proteolytic degradation during purification, and antibiotics may be included to prevent the growth of adventitious contaminants. The TRAF proteins of the present invention are conveniently purified by affinity chromatography, based upon their ability to specifically associate with the intracellular domain of a TNF-R2.

One skilled in the art will appreciate that purification methods suitable for native TRAF may require modification to account for changes in the character of a native TRAF or its variants upon expression in recombinant cell culture.

H. Covalent Modifications of TRAF Polypeptides

Covalent modifications of TRAF are included within the scope herein. Such modifications are traditionally introduced by reacting targeted amino acid residues of the TRAF with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the TRAF, or for the preparation of anti-TRAF receptor antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties*, W.H. Freeman & Co., San Francisco, pp. 79-86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. No. 4,640,835; 4,496,689; 4,301,144; 4,670,417; 4,791,192 or 4,179,337.

Derivatization with bifunctional agents is useful for preparing intramolecular aggregates of the TRAF with polypeptides as well as for cross-linking the TRAF polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The TRAF polypeptides may be linked to various nonproteinaceous polymers, such as polyethylene glycol, polypropylene glycol or polyoxyalkylenes, in the manner set forth in U.S. Pat. No. 4,640,835; 4,496,689; 4,301,144; 4,670,417; 4,791,192 or 4,179,337.

The TRAF may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

I. Glycosylation Variants of the TRAFs

The native TRAFs are believed to be unglycosylated, however, variants having glycosylation are within the scope herein. For ease, changes in the glycosylation pattern of a native polypeptide are usually made at the DNA level, essentially using the techniques discussed hereinabove with respect to the amino acid sequence variants. Thus, glycosylation signals can be introduced into the DNA sequence of native TRAF polypeptides.

Chemical or enzymatic coupling of glycosides to the TRAF molecules of the molecules of the present invention may also be used to add carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep. 1987), and in Aplin and Wriston, *CRC Crit. Rev. Biochem.*, pp. 259-306.

J. Anti-TRAF Antibody Preparation (i) Polyclonal Antibodies

Polyclonal antibodies to a TRAF molecule generally are raised in animals by multiple subcutaneous (sc) or intraperitoneal (ip) injections of the TRAF and an adjuvant. It may be useful to conjugate the TRAF or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to 1/10 the original amount of conjugate in Freud's complete adjuvant by subcutaneous injection at multiple sites. 7 to 14 days later the animals are bled and the serum is assayed for anti-TRAF antibody titer. Animals are boosted until the titer plateaus. Preferably, the animal boosted with the conjugate of the same TRAF, but conjugated to a different protein and/or through a different cross-linking reagent. Conjugates also can be made in recombinant cell culture as protein fusions. Also, aggregating agents such as alum are used to enhance the immune response.

(ii) Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-TRAF monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp. 59-103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., *Monoclonal Antibody Production Techniques and Applications*, pp. 51-63 (Marcel Dekker, Inc., New York, 1987)].

Culture medium in which hybridoma cells are growing is assayed for production of monoclonal antibodies directed against TRAF. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp. 59-104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-TRAF monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a TRAF and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard (which may be a TRAF polypeptide or an immunologically reactive portion thereof) to compete with the test sample analyte (TRAF) for binding with a limited amount of antibody. The amount of TRAF in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

(iii) Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522-525 (1986); Riechmann et al., *Nature* 332, 323-327 (1988); Verhoeyen et al., *Science* 239, 1534-1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed 21 Aug. 1992, which is a continuation-in-part of application Serial No. 07/715,272 filed 14 Jun. 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al, *Proc. Natl. Acad. Sci. USA* 90, 2551-255 (1993); Jakobovits et al., *Nature* 362, 255-258 (1993).

(iv) Bispecific Antibodies

Bispecific antibodies are monoclonal, preferably human or humanized, antibodies that have binding specificities for at least two different antigens. In the present case, one of the binding specificities is for a TRAF, the other one is for any other antigen, and preferably for another receptor or receptor subunit. For example, bispecific antibodies specifically binding two different TRAFs, or a TNF receptor (preferably TNF-R2) and a TRAF, are within the scope of the present invention.

Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed 17 Aug. 1992.

For further details of generating bispecific antibodies see, for example, Suresh et al., *Methods in Enzymology* 121, 210 (1986).

(v) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

L. Use of TRAF Molecules

Based upon their ability to specifically associate with the intracellular domain of TNF-R2, the TRAF molecules of the present invention can be used to purify TNF-R2, which, in turn, is useful in the treatment of various pathological conditions associated with the expression of TNF, such as endotoxic (septic) shock and rheumatoid arthritis (RA). The dose regimen effective in the treatment of these and other diseases can be determined by routine experimentation.

Therapeutic formulations of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., 1983, "Biopolymers" 22 (1): 547-556), poly (2-hydroxyethyl-methacrylate) (R. Langer, et al., 1981, "J. Biomed. Mater. Res." 15: 167-277 and R. Langer, 1982, Chem. Tech." 12: 98-105), ethylene vinyl acetate (R. Langer et al., Id.) or poly-D-(−)-3-hydroxybutyric acid (EP 133,988A). Sustained release compositions also include liposomes. Liposomes containing a molecule within the scope of the present invention are prepared by methods known per se: DE 3,218,121A; Epstein et al., 1985, "Proc. Natl. Acad. Sci. USA" 82: 3688-3692; Hwang et al., 1980, "Proc. Natl. Acad. Sci. USA" 77: 4030-4034; EP 52322A; EP 36676A; EP 88046A; EP 143949A; EP 142641A; Japanese patent application 83-118008; U.S. Pat. Nos. 4,485,045 and 4,544,545; and EP 102,324A. Ordinarily the liposomes are of the small (about 200-800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Typically, the clinician will administer a molecule of the present invention until a dosage is reached that provides the required biological effect. The progress of this therapy is easily monitored by conventional assays.

TRAF molecules may additionally be used to generate blocking (antagonist) or agonist anti-TRAF antibodies, which can be used to block or mimic TNF biological activities mediated (exclusively or partially) by TNF-R2, or to purify other TRAF proteins having an epitope to which the antibodies bind. Methods for generating anti-TRAF antibodies have been described hereinabove. Other TRAF proteins may be identified and purified, for example, by using the "two-hybrid" assay or its modified forms. Thus, factors (including native TRAF proteins and their functional derivatives) that interact with the intracellular domain of TNF-R2 primarily by dimerizing with a TRAF directly binding to that domain (e.g. TRAF2) can be identified by expressing nucleic acid molecules encoding two fusion proteins in a single host cell transfected with nucleic acid encoding a TRAF capable of specific binding the TNF-R2 intracellular domain. Specifically, nucleic acid molecules encoding a first polypeptide comprising a fusion of an intracellular domain sequence of a native TNF-R2 to the DNA-binding domain of a transcriptional activator, and a second polypeptide comprising a fusion of a candidate polypeptide factor to the activation domain of a transcriptional activator are expressed in a single host cell transfected with nucleic acid encoding a polypeptide factor capable of strong specific binding to the intracellular domain of TNF-R2 (e.g. TRAF2), and with nucleic acid encoding a reporter gene. The association of the candidate polypeptide with the intracellular domain of TNF-R2 or with the polypeptide factor capable of binding to the intracellular domain of TNF-R2 is monitored by detecting the polypeptide encoded by the reporter gene.

TRAF molecules (including native TRAF polypeptides and functional derivatives) can further be used in commercial screening assays to identify further molecules that inhibit TNF signaling by disrupting the association of such TRAF molecules with TNF-R2. Such screening assays may, for example, be performed in a two-hybrid assay format as discussed hereinabove.

Further details of the invention will be apparent from the following non-limiting examples.

EXAMPLE 1

Purification of TRAF-1

A. Cell Culture and Biological Reagents

The murine interleukin 2 (IL-2)-dependent cytotoxic T cell line CT6 (Ranges et al. *J. Immunol.* 142, 1203-1208 [1989]) was cultured in RPMI 1640 media supplemented with 10-20 units recombinant human IL-2 (Boehringer Mannheim), 10-15% fetal calf serum (Hyclone), 2 mM L-glutamine, $10^{-5}$ M β-mercaptoethanol, 100 units of penicillin per ml, and 100 μg of streptomycin per ml (GIBCO/BRL). The human T-cell lymphoma line Jurkat was obtained from the American Type Culture Collection (ATCC; Rockville, Md.) and maintained in RPMI 1640 media containing 10% fetal calf serum. The human embryonic kidney cell line 293 (ATCC CRL 1573) and 293 cells overexpressing the hTNF-R2 (293/TNF- R2) were maintained as described (Pennica et al., *J. Biol. Chem.* 267, 21172-21178 [1992]). Recombinant hTNF and recombinant mTNF (specific activity of >$10^7$ units/mg) were provided by the Genentech Manufacturing Group. The rabbit anti-human and anti-murine TNF-R2 antibodies have been described previously (Pennica et al., supra; Tartaglia et al., *J. Biol. Chem.* 267, 4304-4307 [1991]). Anti-human TNF-R1 monoclonal antibody 986 (IgG2a isotype) and anti-human TNF-R2 monoclonal antibodies 1036, 1035 and 1038 (IgG2b, IgG2a and IgG2b isotypes, respectively) were produced as described (Pennica et al., *Biochemistry* 31, 1134-1141 [1992]).

B. Mutational Analysis of the Intracellular Domain of hTNF-R2

Figure 1:
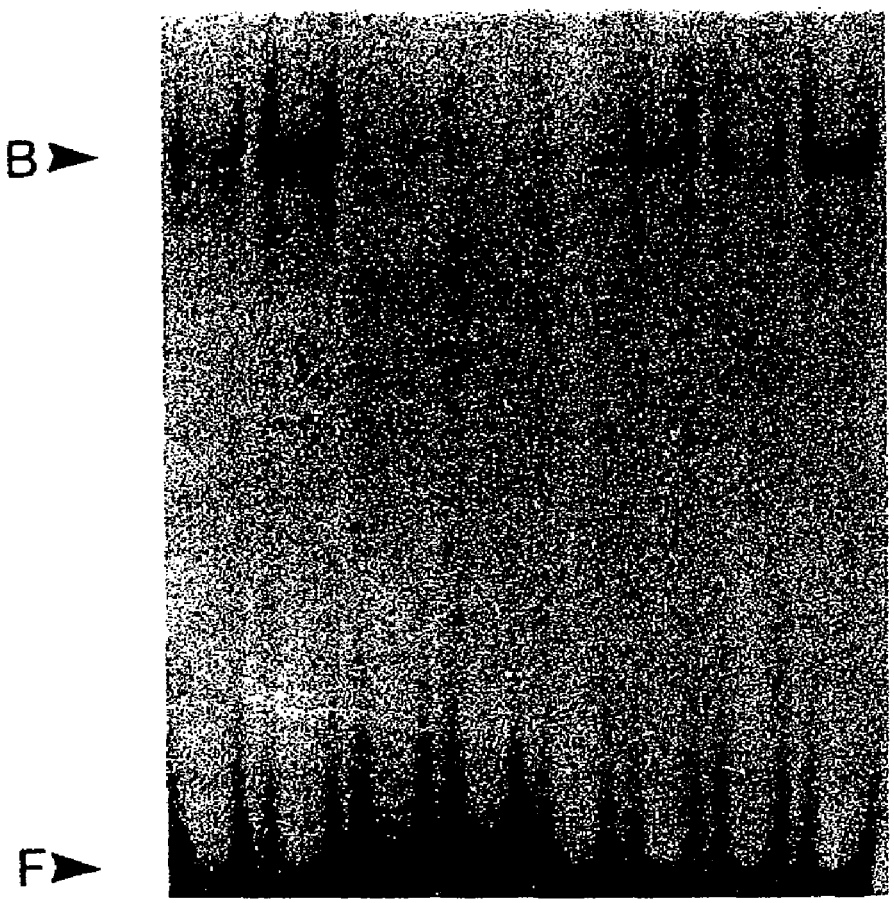
FIG. 1. Activation of the transcription factor NF-kB through TNF-R2 in CT6 cells.

It has been shown that the TNF induced proliferation of murine CT6 cells is mediated by the 75 kd TNF receptor (TNF-R2; Tartaglia et al., 1991, supra). In addition, TNF-R2 activates the transcription factor NF-κB (Lenardo & Baltimore, *Cell* 58: 227-229 [1989]) and mediates the transcriptional induction of the granulocyte-macrophage colony stimulating factor (GM-CSF) gene (Miyatake et al., *EMBO J.* 4, 2561-2568 [1985]; Stanley et al., *EMBO J.* 4, 2569-2573 [1985]) and the A20 zinc finger protein gene (Opipari et al., *J. Biol. Chem.* 265, 14705-14708 [1990]) in CT6 cells (FIG. 1).

To identify sequences within the intracellular domain of the hTNF-R2 (hTNF-R2icd) that are required for TNF signaling a series of mutant hTNF-R2 expression vectors was generated that encode receptors with truncated intracellular domains. DNA fragments containing C-terminally truncated hTNR-R2icds were amplified from the full length expression vector pRK-TNF-R2 (Tartaglia et al., *Cell* 73, 213-216 [1993]) by PCR with Pfu DNA polymerase (Stratagene). PCR was run for 20 cycles (45 s at 95° C.; 60 s at 55° C.; 60 s at 72° C.) after an initial step of 6 min at 95° C. A 0.5 kb DNA fragment encoding an intracellular domain which lacks amino acids 424-439 of the wild type hTNF-R2 was amplified using the oligonucleotide primers 5'-CCTTGTGCCTGCA-GAGAGAAG-3' (SEQ. ID. NO: 23) and 5'-CTAGGT-TAACTTTCGGTGCTCCCCAGCAGGGTCTC-3' (SEQ. ID. NO: 24). The fragment was digested with PstI and HindII, gel purified, and re-cloned into the hTNF-R2 cDNA using the expression vector pRIS (Tartaglia & Goeddel, *J. Biol. Chem.* 267, 4304-4307 [1992]; hTNF-R2(−16)). Similar mutant hTNF-R2 expression vectors were generated that encode receptors lacking amino acids 403-439 (5'-CTAGGT-TAACTGGAGAAGGGGACCTGCTCGTCCTT-3' (SEQ. ID NO: 25); hTNF-R2(−37)), amino acids 381-439 (5'-CTAGGTTAACTGCTGGCTTGGGAGGAGCACTGTGA-3' (SEQ. ID NO: 26); hTNF-R2(−59)), amino acids 346-439 (5'-CTAGGTTAACTGCTCCCGGTGCTGG CCCGGGC-CTC-3' (SEQ. ID NO: 27); hTNF-R2(−94)) and amino acids 308-439 (5'-CTAGGTTAACTGCACTGGCCGAGCTCTC-CAGGGA-3' (SEQ. ID NO: 28); hTNF-R2(−132)). A deletion of amino acids 304-345 of hTNF-R2 was constructed by partial digest of pRK-TNF-R2 with SacI and re-ligation of the vector (hTNF-R2(Δ304-345)). A deletion of the entire intracellular domain of hTNF-R2 was constructed from pRK-TNF-R2 by replacement of sequences between the PstI site adjacent to the transmembrane domain and the ClaI site with a double-stranded oligonucleotide (5'-GTGATGAGAAT-TCAT-3' (SEQ. ID NO: 29) and 5'-CGATGAATTCTC ATCACTGCA-3') (SEQ. ID NO: 30) containing an in-frame stop codon immediately following Gln$^{273}$ (hTNF-R2(−166)). A mutation converting Ser$^{393}$ into Ala was introduced into the hTNF-R2 cDNA by site-directed mutagenesis as described (Tartaglia et al., *Cell* 74, 845-853 [1993]; hTNF-R2 (S393A)). Verification of correctly modified cDNAs was determined by double-strand sequencing using the Sequenase 2.0 Sequencing Kit (U.S. Biochemical).

The expression vectors encoding the intact and truncated hTNF-R2 were introduced into CT6 cells by electroporation. 5×$10^6$ cells in 0.3 ml RPMI 1640 media were cotransfected with 0.5 μg of ScaI-digested pRK.neo (Tartaglia & Goeddel, 1992, supra) and 20 μg of ScaI-digested hTNF-R2 expression vector using the Bio-Rad Gene Pulser with Capacitance Extender (0.4 cm cuvette, 960 μF, 250 V). Electroporated cells were resuspended in 50 ml media and after 2 days plated into 96-well microtiter plates by limiting dilution in selective media containing 100 μg/ml G418 (GIBCO/BRL). After three weeks, individual G418-resistant clones were picked and expanded. Clones that express the hTNF-R2 were identified by FACS analysis as described (Table 1; Pennica et al., *J. Biol. Chem.* 1992, supra).

Proliferation of CT6 clones expressing the full length and truncated hTNF-R2 was measured by [$^3$H]thymidine incorporation as described (Tartaglia et al., *Proc. Natl. Acad. Sci. USA* 88, 9292-9296 [1991]). NF-κB activation was analyzed by electrophoretic mobility shift assay with nuclear extracts prepared from stimulated or unstimulated CT6 cells as described (Schütze et al., *Cell* 71, 765-776 [1992]).

Table 1 shows that the transfected hTNF-R2 signals proliferation and NF-κB activation in CT6 cells. In addition, mutant human receptors which lack the C-terminal 16 amino acids or the internal 42 amino acids 304-345 are still functional in mediating these activities. In contrast, mutant receptors which lack the C-terminal 37 amino acids or contain further C-terminal deletions are defective in these assays. These results indicate that a region of 78 amino acids within the intracellular domain of hTNF-R2 comprising amino acids 346-423 is required for mediating TNF signaling. This region contains a potential protein kinase C phosphorylation site (Ser$^{393}$-Pro$^{394}$-Lys$^{395}$) which is conserved in the murine TNF-R2. However, a mutant hTNF-R2 containing Ala instead of Ser$^{393}$ is biologically functional (Table 1) indicating that this phosphorylation site is not involved in TNF-R2 mediated signaling.

C. Identification of Factors that Associate with the Intracellular Domain of hTNF-R2

To identify factors that are associated with the intracellular domain of hTNF-R2 immunoprecipitation of the receptor from lysates of [$^{35}$S]-labeled transfected CT6 cells was performed. 5×$10^6$ CT6 cells expressing the wild type hTNF-R2 were washed twice with low glucose Dulbecco's modified Eagle's media without cysteine and methionine and incubated in fresh media for 30 min. The cells were seeded into a 100-mm plate in 5 ml media (without cysteine and methionine) containing [$^{35}$S]cysteine and [$^{35}$S]methionine (50 μCi of L-[$^{35}$S]-in vitro cell labeling mix/ml; Amersham). The cells were incubated for 4 h at 37° C., stimulated for 10 min with 100 ng/ml hTNF, harvested, washed twice with cold PBS and lysed for 20 min at 4° C. in 1 ml of 0.1% NP40 lysis buffer containing 50 mM HEPES pH 7.2, 250 mM NaCl, 10% Glycerol, 2 mM EDTA, 1 mM PMSF, 1 μg/ml Benzamidine, 1 μg/ml Aprotinin, 1 μg/ml Leupeptin. Nuclear and cell debris were removed by centrifugation at 10,000×g for 10 min at 4° C. The cell lysate was precleared for 1 h at 4° C. with 50 μl Pansorbin (Calbiochem). The lysate was incubated for 8 h at 4° C. with 1 μg of each of the anti-hTNF-R2 monoclonal antibodies 1035 and 1038 (directed against different epitopes of the extracellular domain of the hTNF-R2) that had been preabsorbed with 1 ml of unlabeled lysate from untransfected CT6 cells and collected with 15 μl of protein A-agarose beads (Oncogene Science). The beads were washed extensively with lysis buffer, resuspended in SDS sample buffer and the supernatant electrophoresed on a 4-12% or 8% Tris/glycine polyacrylamide gel. The gel was fixed, incubated in Amplify (Amersham), dried, and exposed to film at −80° C.

Several bands in the range of 45-50 kd and one band of approximately 68 kd were specifically coprecipitated with the immunoprecipitated hTNF-R2 in CT6 cells (FIG. 2A). The same result was obtained when the hTNF-R2 was immunoprecipitated from unlabeled 293/TNF-R2 cells followed by incubation with labeled lysate from untransfected CT6 cells (FIG. 2B). The pattern of bands coprecipitated with hTNF-R2 was identical regardless of whether the lysate was prepared from cells that had been stimulated with hTNF or left unstimulated, indicating that these proteins are constitutively associated with the hTNF-R2. This is similar to results observed for the tyrosine kinase JAK2 which is associated with the intracellular domain of the erythropoietin receptor (Witthuhn et al., *Cell* 74, 227-236 [1993]).

In order to establish a large scale purification procedure for factors that associate with the hTNF-R2icd, the intracellular domain of hTNF-R2 was expressed as a glutathione S-transferase (GST) fusion protein (Smith & Johnson, 1988, supra). The intracellular domain of hTNF-R2 was amplified from pRK-TNF-R2 by PCR with Pfu DNA polymerase as described above using the oligonucleotide primers 5'-GATCGGATCCAAAAAGAAGCC CTTGTGCCTGCA-3' (SEQ. ID NO: 31) and 5'-GCCTGGTTAACTGGGC-3' (SEQ. ID NO: 32). The amplified 0.55 kb DNA fragment was blunt-ended, digested with BamHI and cloned into BamHI/SmaI-digested pGEX-2TK vector (Pharmacia; pGST-hTNF-R2icd). The pGST-hTNF-R2icd plasmid was transformed into a protease deficient strain of *E. coli* K12 carrying the lacI$^q$ gene on the chromosome (Genentech), an overnight culture diluted 1:10 in fresh LB-medium containing 100 μg/ml carbenicillin and grown at 37° C. for 2 h. After induction with 0.1 mM IPTG, cells were grown for 1 h at 37° C., pelleted and washed once with cold PBS. The cells were resuspended in 1/100 culture volume of resuspension buffer containing 20 mM Tris.HCl pH 7.5, 1 M NaCl, 5 mM EDTA, 1 mM DTT, 1 mM PMSF, 1 μg/ml Benzamidine, 1 μg/ml Aprotinin, 1 μg/ml Leupeptin. After sonication on ice, insoluble material was removed by centrifugation at 10,000×g for 15 min at 4° C. Triton X-100 was added to 1% and the cell lysate incubated for 30 min at room temperature on a rotator with 500 μl of a 50% slurry of glutathione-agarose beads (sulphur linkage; Sigma) in PBS per 1 l culture volume. The beads were collected by brief centrifugation at 500×g and washed extensively with resuspension buffer. An aliquot of the purified GST-hTNF-R2icd fusion protein was analyzed by SDS-PAGE (FIG. 3). Concentrations of 5-8 mg fusion protein/ml of swollen beads were obtained routinely.

To prepare a covalently linked GST-hTNF-R2icd fusion protein affinity matrix, the fusion protein was eluted from glutathione-agarose beads by competition with free glutathione using 3×30 min washes with 1 bead volume of 250 mM Tris.HCl pH 8.0 containing 50 mM reduced glutathione (Sigma). The eluted fusion protein was dialyzed against 0.1 M HEPES pH 7.2, 150 mM NaCl and covalently coupled to Affigel10/15 (2:1 ratio; Bio-Rad) according to the instructions of the manufacturer. Fusion protein concentrations of up to 10 mg/ml of swollen beads were obtained.

Coprecipitation experiments with GST-hTNF-R2icd fusion protein were performed by incubating 3 μl fusion protein beads with 1 ml of cell lysate prepared from [$^{35}$S]-labeled CT6 cells as described above. After 8 h at 4° C. the fusion protein beads were extensively washed with lysis buffer and analyzed by SDS-PAGE and autoradiography. A pattern of bands was found to specifically coprecipitate with the GST-hTNF-R2icd fusion protein either bound to glutathione-agarose beads or covalently coupled to Affigel10/15 (FIG. 4) that was very similar in size to the bands coprecipitating with the immunoprecipitated hTNF-R2 (see FIG. 3). This suggests that the GST-hTNF-R2icd fusion protein expressed in *E. coli* does associate with the same intracellular factors as the wild type hTNF-R2 in CT6 cells.

Expression vectors were made that encode GST-hTNF-R2icd fusion proteins with mutant intracellular domains according to the mutational analysis described above. Using the same strategy as for the wild type hTNF-R2icd DNA fragments encoding the mutant −16, −37, −59 and Δ304-345 hTNF-R2 intracellular domains were amplified by PCR and cloned into the pGEX-2TK vector. In addition, a 0.14 kb DNA fragment was amplified using the oligonucleotide primers 5'-GATCGGATCCGGAGACACAGATTCCA GCCCC-3' (SEQ. ID NO: 51) and 5'-GATCGAATTCTTAACTCT-TCGGTGCTCCCCAGCAG-3' (SEQ. ID NO: 52), digested with BamHI and EcoRI and cloned into pGEX-2TK. This DNA fragment encodes a peptide of 41 amino acids that correspond to amino acids 384-424 of the hTNF-R2icd. The fusion proteins were expressed, purified and assayed for coprecipitating proteins as described above.

As shown in FIG. 5 the GST-hTNF-R2icd fusion proteins containing the intracellular domains of the functional receptor mutants hTNF-R2(−16) and hTNF-R2(Δ304-345) coprecipitated the same bands as the fusion protein containing the wild type hTNF-R2icd. In contrast, the GST-hTNF-R2icd fusion proteins which contain the intracellular domains of the inactive mutants hTNF-R2(−37) and hTNF-R2(−59) did not coprecipitate these bands. This correlation between the biological activity of hTNF-R2s with mutant intracellular domains and the coprecipitation results obtained with the corresponding GST-hTNF-R2icd fusion proteins supports the observation that the wild type GST-hTNF-R2icd fusion protein associates with the same intracellular factors as the immunoprecipitated hTNF-R2.

In addition, the GST-hTNF-R2icd(384-424) fusion protein was able to coprecipitate the bands at 45-50 kd and 68 kd although to a weaker extent than the other fusion proteins (FIG. 5). The 41 amino acids of the hTNF-R2icd contained in this GST-fusion protein are comprised within the 78 amino acids region of the hTNF-R2icd that has been identified to be required for mediating TNF signaling in CT6 cells (see above). This suggests that this short region of the hTNF-R2icd is sufficient to mediate the association of potential signaling molecules with the receptor.

Competition coprecipitation experiments were performed in which the hTNF-R2 was immunoprecipitated from unlabeled 293/TNF-R2 cells and then incubated with labeled CT6 cell lysate that had been precleared with 50 μl of GST-hTNF-R2icd fusion protein beads. Preincubation of the CT6 extracts with GST beads alone or GST-hTNF-R2icd(−37) and GST-hTNF-R2icd(−59) fusion protein beads had no effect on the pattern of proteins coprecipitating with the immunoprecipitated hTNF-R2 (FIGS. 6A-B). However, if the cell lysate had been precleared with GST-hTNF-R2icd or GST-hTNF-R2icd (−16) fusion protein beads, these proteins did not coprecipitate with the immunoprecipitated hTNF-R2 (FIGS. 6A-B), indicating that they had been depleted from the labeled CT6 cell extract by the GST-hTNF-R2icd fusion proteins. This result demonstrates that the wild type GST-hTNF-R2icd fusion protein associates with the same intracellular factors as the immunoprecipitated hTNF-R2. Consequently, this GST-fusion protein material can be used for large scale purification of factors that are associated with the intracellular domain the of hTNF-R2.

Coprecipitation experiments of GST-hTNF-R2icd fusion beads with cell lysate prepared from [$^{35}$S] labeled human Jurkat cells revealed a pattern of coprecipitating proteins very similar in size to the pattern observed with murine CT6 lysates (FIG. 7). This suggests that the TNF-R2 associated factors are closely related between the mouse and human species.

To investigate the subcellular localization of the hTNF-R2 associated factors, cytoplasmic and membrane fractions from CT6 cells were prepared essentially as described (Deutscher, *Methods in Enzymol.* 182: Academic Press, San Diego [1990]). Briefly, [$^{35}$S] labeled CT6 cells were washed once with cold PBS and once with isotonic salt buffer containing 50 mM Tris.HCl pH 7.4, 100 mM NaCl, 1 mM EDTA, 1 mM PMSF, 1 µg/ml Aprotinin and 1 µg/ml Leupeptin. Cells were resuspended in 5 ml isotonic salt buffer, and lysed in a glass douncer (Wheaton) with 20 strokes using the 'B' pestle. Large cell debris were removed by centrifugation at 750×g for 10 min at 4° C. and the supernatant subjected to ultracentrifugation at 100,000×g for 30 min at 4° C. The supernatant which constitutes the cytoplasmic fraction was removed and the pellet resuspended in 50 mM Tris.HCl pH 7.4, 1 mM EDTA, 1 mM PMSF, 1 µg/ml Aprotinin, 1 µg/ml Leupeptin. This crude membrane fraction was layered on a cushion of 35% w/v sucrose in PBS and centrifuged at 30,000×g for 45 min at 4° C. The purified cell membrane fraction at the interface between the sucrose and the buffer phases was removed carefully, concentrated by centrifugation at 100,000×g for 30 min at 4° C. and extracted with 0.1% NP40 lysis buffer for 30 min at 4° C. The cell membrane lysate and the cytoplasmic fraction were used in coprecipitation experiments with GST-hTNF-R2 fusion protein beads as described above.

The factors associating with the hTNF-R2icd were found to be localized in the cytoplasmic cell fraction (FIG. 8). A small amount could also be detected in the purified cell membrane fraction consistent with the observation that these factors are constitutively associated with the hTNF-R2icd (see above).

D. Large Scale Purification

For large scale purification of hTNF-R2icd associated factors 60 l of CT6 cells (3×10$^{10}$ cells) were harvested and washed twice with cold PBS. All subsequent operations were carried out at 4° C. The cells were lysed by adding 120 ml of 0.1% NP40 lysis buffer containing 100 mM NaCl and rocked gently for 30 min. Insoluble material was removed by centrifugation for 10 min at 10,000×g. The supernatant was then centrifuged at 100,000×g for 1 hr and dialyzed against lysis buffer containing 500 mM NaCl. All subsequent purification steps were carried out in lysis buffer containing 500 mM NaCl. The cell lysate was passed through a 15 ml glutathione-agarose GST-hTNF-R2icd(−37) fusion protein preabsorption column. The flow-through was applied to a 0.3 ml Affigel10/15 GST-hTNF-R2icd fusion protein affinity column. For control, the lysate was run through a similar Affigel10/15 GST-hTNF-R2icd(−37) fusion protein affinity column in parallel. After extensive washing, proteins bound to the resins were eluted with five column volumes of ImmunoPure Gentle Ag1Ab Elution Buffer (Pierce) containing, 0.1 M DTT, precipitated with Methanol/Chloroform and resuspended in SDS sample buffer containing 5% SDS. One tenth of the material was separated by SDS-PAGE under reducing conditions and visualized by silver staining (FIG. 9). Protein bands that were specifically eluted from the GST-hTNF-R2icd fusion protein affinity column were observed at approximately 45-50 kd and 68-70 kd.

The remaining purified material was separated by SDS-PAGE, electrophoretically transferred to PVDF sequencing membrane (Millipore) and proteins visualized by staining with R250. The protein band at 45-50 kd (TNF Receptor Associated Factor 1 or TRAF1) was cut out and subjected to amino acid sequence analysis by automated Edman degradation on an Applied Biosystems sequencer. Since the material proved to be N-terminally blocked, internal sequence information was obtained from individual peptides that were purified by reversed phase capillary HPLC after protease digestion prior to sequence analysis. Two peptides that were obtained from trypsin and lysine C digestion, respectively, had the sequences APMALER and KHAYVK (SEQ. ID. NOS: 41 and 42).

EXAMPLE 2

Recombinant Production of TRAF-1

The following degenerate oligonucleotides were designed based on the sequences of the above peptides: BP50-1 sense, 5'-GCNCCNATGGCNYTNGARC/AG (SEQ. ID. NOs: 33-35); BP50-1 antisense, 5'-CT/GYTCNARNGCCATNG-GNGC (SEQ. ID NOs: 36-38); BP50-11 sense, 5'-AAR-CAYGCNTAY GTNAA (SEQ. ID NO: 39); BP50-11 antisense, 5'-TTNACRTANGCRTGYTT (SEQ. ID NO: 40). 1 µg poly(A)$^+$mRNA isolated from CT6 cells was oligo(dT)-primed and reverse transcribed using the cDNA Cycle Kit (Invitrogen) according to the instructions of the manufacturer. First-strand CT6 cDNA was subjected to PCR with combinations of the degenerate oligonucleotides listed above using a Cetus GeneAmp Kit and Perkin-Elmer Thermocycler. The PCR was run for 35 cycles (45 s at 95° C.; 60 s at 55° C.; 150 s at 72° C.) after an initial step of 6 min at 95° C. The PCR products were analyzed by electrophoresis on a 1.6% agarose gel. The PCR reaction obtained with the primer combination BP50-1 sense and BP50-11 antisense Coomanii Brilliant Blue R-250 (Sigma) contained an amplified DNA fragment of approximately 0.75 kb. This fragment was gel-purified, subcloned into pBluescript KS (Stratagene), and sequenced.

A 0.65 kb PstI DNA fragment was isolated from the cloned PCR fragment and labeled with [λ-$^{32}$P]dCTP using the T7 Quick Prime Kit (Pharmacia). The labeled fragment was used to screen approximately 1×10$^6$ recombinant phage clones from a CT6 cDNA library that had been constructed in λgt22a using the Supercript Lambda System For cDNA Synthesis And λ Cloning (GIBCO/BRL) according to the instructions of the manufacturer. Hybridization and washing of the filters were carried out under high-stringency conditions according to standard protocols (Ausubel et al., *Current Protocols in Molecular Biology*, Green Publishing Associates and Wiley Interscience, New York 1987). Four positive clones were plaque-purified by a secondary screen. The cDNA inserts of these phage clones were subcloned into pBluescript KS and sequenced on both strands (FIGS. 10A-B). The longest of the cDNAs was found to be 2 kb. The other three cDNA clones represented truncated versions of the 2 kb cDNA clone. The 2 kb cDNA clone contained an open reading frame encoding a protein of 409 amino acids (FIGS. 10A-B). Within the predicted protein were the sequences APMALER (SEQ. ID. NO: 41) and KHAYVK (SEQ. ID. NO: 42), as well as the sequences PGSNLGS (SEQ. ID. NO: 43) and KDDTMFLK (SEQ. ID. NO: 44) which correspond to two other peptide sequences obtained from protein sequence analysis. These results confirm that the isolated 2 kb cDNA clone encodes the purified TRAF1.

To analyze similarities between TRAF1 and other known sequences, the TRAF1 sequence was searched against the Genentech protein database. No obvious similarity of significance between TRAF1 and any other known protein was found, indicating that TRAF1 is a novel molecule.

EXAMPLE 3

Identification and Cloning of TRAF2

To directly isolate genes coding for proteins that associate with the intracellular domain of TNF-R2 the yeast two-hybrid system for the detection of protein-protein interactions (Fields & Song, Nature 340, 245-246 [1989]) was used. The intracellular domain of hTNF-R2 was amplified from pRK-TNF-R2 by PCR with Pfu DNA polymerase as described above using the oligonucleotide primers 5'-TCG ATCGTCGACCAAAAAGAAGCCCTCCTGCCTACAA-3' (SEQ. ID NO: 45) and 5'-CTAGAGATCTCAGG GGTCAG-GCCACTTT-3' (SEQ. ID. NO: 46). The amplified 0.55 kb DNA fragment was digested with SalI and BglII, gel-purified and cloned into the GAL4 DNA-binding domain vector pPC97 (Chevray & Nathans, 1992, supra; pPC97-hTNF-R2icd). Similar constructs were made containing the GAL4 DNA-binding domain fused to the hTNF-R2icd(-16) (5'-CTAGA GATCTGTTAACTTTCGGTGCTCCCCAG-CAGGGTCTC-3' (SEQ. ID. NO: 47); pPC97-hTNF-R2icd (-16)), the hTNF-R2icd(-37) (5'-CTAGAGATCTGTTAACTGGAGAAGGGGACCTGCTCGTCCTT-3' (SEQ. ID. NO: 48); pPC97-hTNF-R2icd(-37)), the hTNF-R2icd(-59) (5'-CTAGAGATCTGTTAACTGC TGGCTTGGGAGGAGCACTGTGA-3' (SEQ. ID. NO: 49); pPC97-hTNF-R2icd(-59)) and the intracellular domain of the murine TNF-R2 (5'-TCGATCGTCGACCAAAAA-GAAGCCCTCCTGCCT ACAA-3' (SEQ. ID NO: 45).5'-CTAGAGATCTCAGGGGTCAGGCCACTTT-3' (SEQ. ID NO: 46); pPC97-mTNF-R2icd).

A plasmid cDNA library in the GAL4 transcriptional activation domain vector pPC86 (Chevray & Nathans, 1992, supra) was constructed from SalI/NotI-adapted, double-stranded fetal liver stromal cell line 7-4 cDNA (a gift of B. Bennett and W. Matthews) as described (Chevray & Nathans, 1992, supra). Plasmid DNA was isolated directly from $2 \times 10^6$ transformed E. coli DH10B (GIBCO/BRL) colonies.

S. cerevisiae HF7c (Clontech) was sequentially transformed with pPC97-hTNF-R2icd and 250 μg library plasmid DNA as described in the Matchmaker Two-Hybrid System (Clontech). The final transformation mixture was plated onto 50 150-mm synthetic dextrose agar plates lacking L-tryptophan, L-leucine, L-histidine and containing 20 mM 3-aminotriazole (Sigma). A total of $2 \times 10^6$ transformed colonies were plated. After 4 days at 30° C. 42 surviving His$^+$-colonies were obtained of which 15 were positive in a filter assay for b-galactosidase activity (Breeden & Nasmyth, Regulation of the Yeast HO gene. Cold Spring Harbor Symposia on Quantitative Biology 50, 643-650, Cold Spring Harbor Laboratory Press, New York, 1985). Yeast DNA was prepared (Hoffmann and Winston, Gene 57, 267-272 [1987]), transformed into E. Coli DH10B by electroporation and colonies containing the pPC86 library plasmid identified by restriction analysis. 14 out of 15 cDNA inserts had a similar size of approximately 2.1 kb. Restriction analysis with DdeI revealed them to be independent cDNA clones derived from the same mRNA species.

Retransformation of three representative cDNA clones into HF7c cells with pPC97 and pPC97-hTNF-R2icd, respectively, confirmed that the encoded GAL4 activation domain fusion proteins do not interact with the GAL4 DNA-binding domain alone but only with the GAL4 DNA-binding hTNF-R2icd fusion protein. The 2.1 kb cDNA insert of one representative clone (pPC86Y17) was sequenced on both strands (FIGS. 11A-B). In addition, the 5'- and 3'-regions of 6 other independent cDNA clones were sequenced confirming that they were derived from the same mRNA species. All clones were shown to be fused to the GAL4 DNA-binding domain in the same reading frame within 20 nucleotides of each other.

Two additional cDNA clones were isolated from a CT6λ phage cDNA library (see above) and 5 additional clones from a mouse liver λ phage cDNA library (Clontech) using a [$^{32}$P]-labeled 0.5 kb PstI DNA fragment from the 5'-region of the pPC86Y17 cDNA insert as hybridization probe. None of these cDNA inserts extended the 5'-sequence of the pPC86 cDNA inserts. Furthermore, the size of the pPC86 cDNA inserts corresponds closely to the size of the actual message as revealed by northern blot analysis of CT6 mRNA (see below). These findings indicate that the cDNA inserts isolated with the two-hybrid system represent full length clones and that the fusion to the GAL4 DNA-binding domain occurred in a very short 5'-untranslated region in-frame with the initiator ATG at position 30 of the pPC86Y17 cDNA insert (see also below). The cDNA clones contain an open reading frame encoding a protein of 501 amino acids (TNF Receptor Associated Factor 2 or TRAF2; FIGS. 11A-B).

A homology search of the TRAF2 sequence against the Genentech protein database revealed that TRAF2 is a novel protein containing an N-terminal RING finger sequence motif (Freemont et al., Cell 64, 483-484 [1991]; Haupt et al., Cell 65, 753-763 [1991]; Inoue et al., supra; FIG. 12A). This sequence motif has been observed in the N-terminal domain of a number of regulatory proteins and is thought to form two zinc-binding finger structures that appear to be involved in protein-DNA interactions (Freemont et al., supra; Haupt et al., supra; Reddy et al., Trends Biochem. Sci. 17, 344-345 [1992]). Members of the RING finger family are putative DNA-binding proteins, some of which are implicated in transcriptional regulation, DNA repair, and site-specific recombination (see FIG. 12A). In addition, the RING finger motif and other zinc-binding sequence motifs have been discussed to be involved in protein-protein interactions (Freemont et al., supra; Haupt et al., supra; Berg, J. Biol. Chem. 265, 6513-6516 [1990]). The importance of this structural motif in TRAF2 is supported by the finding that all GAL4 DNA-binding domain TRAF2 fusions isolated contain the complete N-terminus of TRAF2 (see above). This suggests that the N-terminal RING finger domain of TRAF2 is involved in the interaction with the intracellular domain of TNF-R2.

In addition, TRAF2 shares sequence similarity with the zinc finger motif of Xenopus TFIIIA-type zinc finger proteins (Miller et al., EMBO J. 4, 1609-1614 [1985]; Berg, supra; FIG. 12B). TFIIIA-like zinc finger motifs have also been observed in the RING finger proteins RAD 18 and UVS-2 (FIGS. 12A-B).

No obvious similarity of significance between the C-terminal domain of TRAF2 and any other known protein was found. A comparison of the sequences of TRAF1 and TRAF2 revealed that they share a high degree of amino acid identify in their C-terminal domains (53% identity over 230 amino acids; FIG. 13). Both proteins constitute members of a new family of proteins that contain a novel sequence homology motif, the "TRAF domain". The less conserved N-terminal regions within the TRAF domains of TRAF1 and TRAF2 can potentially form leucine zipper-like structures (FIGS. 10A-B, 11A-B, 13). The leucine zipper is a α-helical structure originally found in a number of DNA-binding proteins that contain leucines occurring at intervals of every seventh amino acid (Landschulz et al., *Science* 240, 1759-1764 [1988]; Vinson et al., *Science* 246, 911-916 [1989]). This structure mediates protein dimerization by intermolecular interaction of the leucine side-chains. Leucine zipper structures have also been predicted for two other RING finger family members, the SS-A/Ro ribonucleoprotein and the gene product of the c-cbl proto-oncogene (see FIGS. 12A-B). The N-terminal domains of TRAF1 and TRAF2 are unrelated, especially with regard to the RING finger domain of TRAF2.

EXAMPLE 4

Functional Analysis of TRAF1 and TRAF2

Hydropathy profiles (Kyte & Doolittle, 1982, supra) of TRAF1 and TRAF2 (FIGS. 14A-B) suggest that they lack signal sequences as well as obvious transmembrane regions and are overall hydrophilic. They are thus likely to represent intracellular proteins which is in accordance with the cytoplasmic localization of TRAF1 as determined experimentally (see above).

Poly(A)$^+$mRNA was prepared from CT6 cells (Badley et al., *Current Opinion in Structural Biology* 3, 11-16, [1988]). Northern analysis (Sambrook et al., 1989, supra) using a radiolabeled TRAF2 hybridization probe as described above indicated that TRAF2 is expressed as a 2.1 kb message in CT6 cells (FIG. 15A). Similarly, TRAF1 is expressed in CT6 cells as a 2 kb message (FIG. 15A).

To examine the tissue distribution of TRAF1 and TRAF2 mRNA, mouse multiple tissue Northern blots (Clontech) were hybridized with radiolabeled TRAF1 and TRAF2 probes according to the instructions of the manufacturer. TRAF2 is expressed constitutively in all mouse tissues examined (heart, brain, spleen, lung, liver, skeletal muscle, kidney and testis; FIG. 15B). The highest expression level was observed in spleen. In contrast, TRAF1 displayed a tissue specific expression. TRAF1 mRNA could only be detected in spleen, lung and testis (FIG. 15B).

Cotransformation of pPC86Y17 (pPC86TRAF2) into HF7c cells with the above described GAL4 DNA-binding TNF-R2icd fusion constructs showed that TRAF2 interacts with the wild type intracellular domains of both the human and the murine TNF-R2 and with the intracellular domain of the biologically active mutant hTNF-R2(−16) (Table 2). However it does not interact with the GAL4 DNA-binding domain alone nor with the intracellular domains of the biologically inactive mutants hTNF-R2(−37) and hTNF-R2(−59). This is in agreement with the results obtained from coprecipitation experiments with wild type and mutant GST-hTNF-R2icd fusion proteins in CT6 cell extracts (see above).

An expression vector encoding a GST-TRAF2 fusion protein was constructed. The TRAF2 coding region was amplified from pPC86TRAF2 by PCR with Pfu DNA polymerase as described above using the oligonucleotide primers 5'-GATCGGATCCTTGTGGTGTGTGGGGG TTGT-3' (SEQ. ID. NO: 53) and 5'-CCTGGCTGGCCTAATGT-3' (SEQ. ID. NO: 54). The amplified 1.6 kb DNA fragment was blunt-ended using *E. coli* DNA polymerase I, digested with BamHI and cloned into BamHI/SmaI-digested pGEX-2TK vector. The GST-TRAF2 fusion protein was expressed in the presence of 1 mM ZnCL$_2$ and purified as described above. GST and GST-TRAF2 fusion protein beads were incubated with lysates from 293 and 293/TNF-R2 cells, and analyzed by SDS-PAGE and Western blot analysis (Sambrook et al., "Molecular Cloning: A Laboratory Manual. Cold Spring Harbor Laboratory Press, N.Y. [1989]) using the ECL detection reagent (Amersham). Primary antibodies directed against the extracellular domains of hTNF-R2 and hTNF-R1 (as a control) were used at a concentration of 0.5 μg/ml and the secondary sheep anti-mouse horseradish peroxidase conjugate (Amersham) at a dilution of 1:6000. As shown in FIG. 16, the GST-TRAF2 fusion protein coprecipitates the hTNF-R2 in 293 cell extracts, thus confirming the results obtained from two hybrid analysis.

To test for possible homo- and heteromeric protein-protein interactions between TRAF1, TRAF2 and the intracellular domain of TNF-R2 the 2.1 kb cDNA insert of pPC86TRAF2 was excised by digestion with SalI and NotI and cloned into pPC97 (pPC97TRAF2). The TRAF1 coding and 3'-untranslated region was amplified from the full length TRAF1 cDNA clone in pBluescript KS by PCR with Pfu DNA polymerase as described above using the T7 sequencing primer (Stratagene) and the oligonucleotide primer 5'-TCGATCGTCGACCGC-CTCCAGCTCAGCCCCTGAT-3' (SEQ. ID. NO: 50). The amplified 1.7 kb DNA fragment was digested with SalI and NotI, gel-purified and cloned into both pPC97 and pPC86 (pPC97TRAF1; pPC86TRAF1).

Cotransformation of pPC86TRAF1 into HF7c cells with the GAL4 DNA-binding TNF-R2 fusion constructs encoding the wild type human and murine intracellular domains indicated that the direct interaction between TRAF1 and the intracellular domain of TNF-R2 is weak (Table 2). However, cotransformation of pPC97TRAF1 and pPC86TRAF2 or pPC97TRAF2 and pPC86TRAF1 revealed that TRAF1 and TRAF2 interact with each other (Table 2) suggesting that a heterodimeric complex of TRAF1 and TRAF2 is associated with the intracellular domain of TNF-R2. Subsequently yeast vectors were constructed in which TRAF2 is expressed directly, i.e. not as a GAL4 fusion protein. pPC97TRAF2 was digested with HindIII and SalI to release a 0.5 kb DNA fragment encoding the GAL4 DNA-binding domain, end-filled with Klenow enzyme, gel-purified, and re-ligated (pPC-TRAF2). In addition, TRAF2 was amplified from pPC86TRAF2 with Pfu DNA polymerase as described above using the oligonucleotide primers 5'-GATCGACTCGAGAT-GCCCAAGAAGAAGCGGAAGGTGGC TGCAGCCAGT-GTGACTTCCCCT-'3 (SEQ. ID. NO:55) and 5'-CTCTGGC-GAAGAAGTCC-3' (SEQ. ID. NO:56). The amplified 2.1 kb DNA fragment was digested with XhoI, end-filled with Klenow enzyme, digested with NotI, gel-purified and cloned into pPC97 that had been digested with HindIII, end-filled and digested with NotI (pPCTRAF2NLS). This expression vector encodes the simian virus 40 large tumor antigen nuclear localization signal (met-pro-lys-lys-lys-arg-lys-val; compare Chevray & Nathans, 1992) fused to the N-terminus of TRAF2. Transformation of pPCTRAF2NLS but not pPC-TRAF2 into HF7c cells harboring the plasmids pPC86TRAF1 and pPC97hTNF-R2icd or pPC97 mTNF-R2icd complemented the histidine deficiency of the host cells (Table 3). This result confirms that a heterodimeric complex of TRAF1 and TRAF2 interacts with the intracellular domain of TNF-R2. In this protein complex mainly TRAF2 contacts the receptor directly potentially through interaction of its RING finger domain with the C-terminal region of the intracellular domain comprising amino acids 304-345 of the human TNF-R2 as suggested from mutational analysis and coprecipitation experiments (see above). TRAF1 and TRAF2 can also form homodimeric complexes as shown by cotransformation of pPC97TRAF1 and pPC86TRAF1 or pPC97TRAF2 and pPC86TRAF2 (Table 2). These results suggest that the homologous C-terminal domains of TRAF1 and TRAF2 represent a novel protein dimerization motif. In analogy, the C-terminal domain of the RING finger protein COP1 from *Arabidopsis thaliana* contains a region with homology to the β subunit of trimeric G proteins that has been discussed to be involved in protein-protein recognition (Deng et al., *Cell* 71, 791-801 [1992]).

Based on the tissue specific expression of TRAF1 (see above), the formation of a heteromeric complex between TRAF1 and TRAF2 can only occur in certain mouse tissues such as spleen, lung and testis. This raises the possibility of other TRAF domain proteins as tissue specific dimerization partners for the constitutively expressed TRAF2. Such tissue specific heterocomplexes with potentially different biological activities could determine different TNF responses mediated by TNF-R2 in various tissues.

To generate antibodies directed specifically against TRAF1 and TRAF2 the N-terminal domains of both proteins were expressed in E. coli as 6xhis tag fusions using the QIAexpress system (Qiagen). A DNA fragment encoding amino acids 2-181 of TRAF1 was amplified from the full length cDNA clone in pBluescript KS by PCR with Pfu DNA polymerase as described above using the oligonucleotide primers 5'-GATCGGATCCGCCTCCAGCTCAGCCCCT-GAT-3' (SEQ. ID. NO:57) and 5'-GATCGGATCCAGCCAG-CAGCTTCTCCTTCAC-3' (SEQ. ID. NO:58). The amplified 0.55 kb DNA fragment was digested with BamHI and cloned into BamHI-digested pQE12 vector (Qiagen). Transformants containing the correct orientation of the DNA insert in the expression vector were determined by restriction analysis (pQETRAF1). Similarly, a DNA fragment encoding amino acids 1-162 of TRAF2 was amplified from pPC86TRAF2 using the oligonucleotide primers 5'-GATCGGATCCT-TGTGGTGTGTGGGGGTTGT-3' (SEQ. ID. NO:53) and 5'-GATCGGATCCGCTCAGG CTC TTTTGGGGCA-3' (SEQ. ID. NO:59), digested with BamHI and cloned into BamHI-digested pQE12 vector (pQETRAF2).

Plasmids pQETRAF1 and pQETRAF2 were transformed into E. coli M15-[pREP4] (Qiagen). The cells were grown, induced, harvested, and the 6xhis tag TRAF1 and TRAF2 fusion proteins purified by Ni-NTA affinity chromatography (Qiagen) under denaturing conditions according to the instructions of the manufacturer. The purified TRAF1 and TRAF2 fusion proteins were resolved on a 13% Tris/glycine polyacrylamide gel, stained with 0.05% Coomassie Brilliant Blue R-250 solution in water, and the appropriate bands excised. Gel slices containing 100-200 µg TRAF1 or TRAF2 fusion protein were used for the immunization of rabbits.

TABLE 1

Analysis of CT6 Clones Expressing Human TNF-R2 Mutants

| CT6 Clone | hTNF-R2 Expression (mean fluorescence) | [³H]Thymidine Incorporation (fold stimulation) | NF-κB Activation |
|---|---|---|---|
| neo.26 | 157 | 0.9 | − |
| hR2.30 | 303 | 3.4 | + |
| hR2.31 | 350 | 4.7 | + |
| −16.25 | 464 | 10.7 | + |
| −16.31 | 465 | 5.1 | + |
| −37.4 | 478 | 1.1 | − |
| −37.20 | 439 | 1.0 | − |
| −59.1 | 276 | 1.3 | − |
| −59.23 | 374 | 1.0 | − |
| −94.5 | 515 | 0.7 | − |
| −94.6 | 477 | 1.0 | − |
| −132.3 | 296 | 1.1 | − |
| −132.22 | 344 | 1.0 | − |
| −166.10 | 361 | 1.0 | − |
| −166.13 | 318 | 1.0 | − |
| Δ304-345 | 469 | nd | + |
| S393A.2 | 407 | 2.9 | nd |
| S393A.8 | 531 | 5.5 | nd |

Expression vectors encoding the intact and truncated hTNF-R2 were transfected into CT6 cells. The expression levels of wild type or mutant receptors of individual CT6 clones were analyzed by flow cytometry and values are expressed as mean fluorescence. For functional analysis two independent CT6 clones were examined for each hTNF-R2 mutant except hTNF-R2(Δ304-345) which represents a pool of sorted cells. Proliferation was measured by [³H]thymidine incorporation of cells that had been treated for 24 hr with a 1:1000 dilution of anti-hTNF-R2 polyclonal antibody. Values are expressed as fold stimulation compared with cells that had been treated with an irrelevant antibody. Data shown are the means of triplicate determinations. Standard deviations were generally less than 5%. NF-κB activation was analyzed by electrophoretic mobility shift assay with nuclear extracts prepared from cells that had been stimulated for 20 min with a 1:500 dilution of anti-hTNF-R2 polyclonal antibody. A plus sign indicates the induction of NF-κB DNA-binding activity compared with nuclear extracts prepared from cells that had been treated with an irrelevant antibody. All CT6 clones retained the ability to induce proliferation and NF-κB activation through the endogenous murine TNF-R2 (data not shown). nd, not determined.

TABLE 2

Interaction between TRAF1, TRAF2 and the Intracellular Domain of TNF-R2

| Transformant | | Growth on trp- leu⁻ medium | Growth on trp- leu⁻ his⁻ medium |
|---|---|---|---|
| DNA-binding domain hybrid | Activation-domain hybrid | | |
| GAL4(DB) | GAL4(TA) | + | − |
| GAL4(DB)-hTNF-R2icd | GAL4(TA) | + | − |
| GAL4(DB)-mTNF-R2icd | GAL4(TA) | + | − |
| GAL4(DB)-hTNF-R2icd (−16) | GAL4(TA) | + | − |
| GAL4(DB)-hTNF-R2icd (−37) | GAL4(TA) | + | − |
| GAL4(DB)-hTNF-R2icd (−59) | GAL4(TA) | + | − |
| GAL4(DB) | GAL4(TA)-TRAF1 | + | − |
| GAL4(DB) | GAL4(TA)-TRAF2 | + | − |
| GAL4(DB)-hTNF-R2icd | GAL4(TA)-TRAF1 | + | −/+ |
| GAL4(DB)-mTNF-R2icd | GAL4(TA)-TRAF1 | + | −/+ |
| GAL4(DB)-hTNF-R2icd | GAL4(TA)-TRAF2 | + | + |
| GAL4(DB)-mTNF-R2icd | GAL4(TA)-TRAF2 | + | + |
| GAL4(DB)-hTNF-R2icd (−16) | GAL4(TA)-TRAF2 | + | + |
| GAL4(DB)-hTNF-R2icd (−37) | GAL4(TA)-TRAF2 | + | − |
| GAL4(DB)-hTNF-R2icd (−59) | GAL4(TA)-TRAF2 | + | − |
| GAL4(DB)-TRAF1 | GAL4(TA) | + | − |
| GAL4(DB)-TRAF2 | GAL4(TA) | + | − |
| GAL4(DB)-TRAF1 | GAL4(TA)-TRAF1 | + | + |
| GAL4(DB)-TRAF1 | GAL4(TA)-TRAF2 | + | + |
| GAL4(DB)-TRAF2 | GAL4(TA)-TRAF2 | + | + |
| GAL4(DB)-TRAF2 | GAL4(TA)-TRAF1 | + | + |

HF7c cells were cotransformed with plasmids (see text) encoding various GAL4 DNA-binding domain (DB) and GAL4 transcriptional activation domain (TA) fusion proteins as indicated. Aliquots of the same transformation mixture were plated onto synthetic dextrose plates lacking trp and leu and plates lacking trp, leu, his and containing 20 mM 3-aminotriazole. Plus signs indicate growth of transformed yeast colonies on the respective plates. Very similar numbers of transformants from the same transformation mixture (90-100%) were obtained on plates lacking trp, leu, his and on plates lacking trp and leu only. Minus/plus signs indicate that the number of transformants growing on plates lacking trp, leu, his was approximately 1-2% of the number of colonies obtained from the same transformation mixture on plates lacking trp and leu only. Filter assays for β-galactosidase activity were performed on colonies growing on plates lacking all three amino acids. All colonies developed a blue color (data not shown).

TABLE 3

Interaction between TRAF1, TRAF2 and the Intracellular Domain of TNF-R2 (continued)

| Transformant | | | Growth on trp- leu- his- medium |
|---|---|---|---|
| DNA-binding domain hybrid | Activation-domain hybrid | Direct expression | |
| GAL4(DB) | GAL4(TA)-TRAF1 | | - |
| GAL4(DB) | GAL4(TA)-TRAF1 | NLS-TRAF2 | - |
| GAL4(DB) | GAL4(TA)-TRAF1 | TRAF2 | - |
| GAL4(DB)-hTNF-R2icd | GAL4(TA)-TRAF1 | | -/+* |
| GAL4(DB)-hTNF-R2icd | GAL4(TA)-TRAF1 | NLS-TRAF2 | + |
| GAL4(DB)-hTNF-R2icd | GAL4(TA)-TRAF1 | TRAF2 | -/+* |
| GAL4(DB)-mTNF-R2icd | GAL4(TA)-TRAF1 | | -/+* |
| GAL4(DB)-mTNF-R2icd | GAL4(TA)-TRAF1 | NLS-TRAF2 | + |
| GAL4(DB)-mTNF-R2icd | GAL4(TA)-TRAF1 | TRAF2 | -/+* |

HF7c cells were sequentially transformed with plasmids (see text) encoding the indicated GAL4 DNA-binding domain (DB) fusion proteins, the GAL4 transcriptional activation domain (TA) TRAF1 fusion protein, and TRAF2 or TRAF2 fused to the simian virus 40 large tumor antigen nuclear localization signal (NLS). The final transformation mixtures were plated onto synthetic dextrose plates lacking trp, leu, his and containing 20 mM 3-aminotriazole. Plus signs indicate growth of transformed yeast colonies on the respective plates.
*See Table 2.

While the invention has necessarily been described in conjunction with preferred embodiments and specific working examples, one of ordinary skill, after reading the foregoing specification, will be able to effect various changes, substitutions or equivalents, and alterations to the subject matter set forth herein, without departing from the spirit and scope herein. Hence, the invention can be practiced in ways other than those specifically described herein. All such modifications are intended to be within the scope of the present invention.

All references cited herein and the references cited therein are hereby expressly incorporated by reference.

The invention claimed is:

1. An antibody capable of specific binding to a native tumor necrosis factor receptor associated factor (TRAF) polypeptide consisting of an amino acid sequence selected from the group consisting of:
   (a) amino acid residues 180 to 409 of TRAF1 of SEQ. ID. NO: 2; and
   (b) amino acid residues 2-181 of TRAF1 of SEQ. ID. NO: 2.

2. A hybridoma cell line producing the antibody of claim 1.

* * * * *